(12) United States Patent
Arai et al.

(10) Patent No.: US 11,701,069 B2
(45) Date of Patent: Jul. 18, 2023

(54) CONTROL DEVICE, RADIOGRAPHY SYSTEM, MEDICAL IMAGING SYSTEM, CONTROL METHOD, AND CONTROL PROGRAM

(71) Applicant: FUJIFILM CORPORATION, Tokyo (JP)

(72) Inventors: Takahisa Arai, Kanagawa (JP); Masakazu Fukuyo, Kanagawa (JP); Takeyasu Kobayashi, Kanagawa (JP); Shunsuke Kodaira, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 0 days.

(21) Appl. No.: 16/794,243

(22) Filed: Feb. 19, 2020

(65) Prior Publication Data
US 2020/0275897 A1  Sep. 3, 2020

(30) Foreign Application Priority Data

Feb. 28, 2019  (JP) .............................. JP2019-036751

(51) Int. Cl.
*A61B 6/04* (2006.01)
*A61B 6/00* (2006.01)
(Continued)

(52) U.S. Cl.
CPC .......... *A61B 6/0435* (2013.01); *A61B 6/0414* (2013.01); *A61B 6/5247* (2013.01);
(Continued)

(58) Field of Classification Search
CPC ... A61B 6/0435; A61B 6/0414; A61B 6/5247; A61B 8/0825; A61B 8/4427;
(Continued)

(56) References Cited

U.S. PATENT DOCUMENTS

2014/0135623 A1* 5/2014 Manak .................. A61B 6/502
600/427
2016/0120407 A1* 5/2016 Martinez-Lorenzo ......................
A61B 5/0507
600/427
(Continued)

FOREIGN PATENT DOCUMENTS

EP         3342350 A2     7/2018
JP       2009-28381 A     2/2009
(Continued)

OTHER PUBLICATIONS

Extended European Search Report dated Jun. 29, 2020, issued in corresponding EP Patent Application No. 20158331.7.
(Continued)

*Primary Examiner* — Keith M Raymond
*Assistant Examiner* — Sean A Frith
(74) *Attorney, Agent, or Firm* — Solaris Intellectual Property Group, PLLC

(57) ABSTRACT

A mammography apparatus includes a compression control unit that, in a case in which continuous imaging that captures a radiographic image of the breast compressed by a compression plate and then captures an ultrasound image of the breast while maintaining the compressed state is performed, performs control to set a force of the compression plate compressing the breast to a first force in the capture of the radiographic image and to change the force of the compression plate compressing the breast from the first force to a second force lower than the first force in the capture of the ultrasound image.

14 Claims, 12 Drawing Sheets

(51) Int. Cl.
*A61B 8/08* (2006.01)
*A61B 8/00* (2006.01)

(52) U.S. Cl.
CPC .......... *A61B 8/0825* (2013.01); *A61B 8/4427* (2013.01); *A61B 8/5261* (2013.01); *A61B 2562/0247* (2013.01); *A61B 2562/0252* (2013.01)

(58) Field of Classification Search
CPC .......... A61B 8/5261; A61B 2562/0247; A61B 2562/0252
See application file for complete search history.

(56) References Cited

U.S. PATENT DOCUMENTS

| 2016/0166217 A1* | 6/2016 | Davis | A61B 8/4416 378/37 |
| 2016/0292851 A1* | 10/2016 | Hamauzu | G06T 5/002 |
| 2017/0367674 A1* | 12/2017 | Arai | A61B 6/42 |
| 2017/0367675 A1* | 12/2017 | Arai | A61B 6/502 |

FOREIGN PATENT DOCUMENTS

| JP | 2010-253245 A | 11/2010 |
| JP | 2012-170718 A | 9/2012 |
| JP | 2017-225633 A | 12/2017 |
| JP | 2017-225634 A | 12/2017 |
| JP | 2017-225635 A | 12/2017 |

OTHER PUBLICATIONS

English language translation of the following: Office action dated Dec. 14, 2021 from the JPO in a Japanese patent application No. 2019-036751 corresponding to the instant patent application.
English language translation of the following: Office action dated Jun. 14, 2022 from the JPO in a Japanese patent application No. 2019-036751 corresponding to the instant patent application.

* cited by examiner

CONTROL DEVICE, RADIOGRAPHY SYSTEM, MEDICAL IMAGING SYSTEM, CONTROL METHOD, AND CONTROL PROGRAM

CROSS-REFERENCE TO RELATED APPLICATION

This application claims priority from Japanese Patent Application No. 2019-036751, filed Feb. 28, 2019, the disclosure of which is incorporated herein by reference in its entirety.

BACKGROUND

Technical Field

The present disclosure relates to a control device, a radiography system, a medical imaging system, a control method, and a non-transitory storage medium storing a control program.

Related Art

A radiography apparatus has been known which irradiates an object, such as the breast of a subject, with radiation emitted from a radiation source and detects the radiation transmitted through the object with a radiation detector to capture a radiographic image.

In addition, an ultrasonography apparatus has been known which scans the breast of a subject using an ultrasound probe and scans the breast with ultrasonic waves to capture an ultrasound image of the breast.

JP2009-028381A and JP2012-170718A disclose an apparatus that can capture both a radiographic image and an ultrasound image of the breast. In JP2009-028381A and JP2012-170718A, the radiographic image and the ultrasound image are captured in a state in which the breast is compressed.

In general, in a case in which the breast is compressed by a compression member, the subject feels pain. In a case in which the radiographic image and the ultrasound image are continuously captured as in the technique disclosed in JP2009-028381A and JP2012-170718A, the time for which the subject feels pain may increase since the time for which the breast is compressed increases. Therefore, a technique for effectively relieving the pain of the subject is required.

SUMMARY

The present disclosure has been made in view of the above-mentioned problems and an object of the present disclosure is to provide a control device, a radiography system, a medical imaging system, a control method, and a non-transitory storage medium storing a control program that may effectively relieve the pain of a subject.

In order to achieve the object, according to a first aspect of the present disclosure, there is provided a control device comprising: a compression control unit that, in a case in which continuous imaging that captures a radiographic image of a breast compressed by a compression member and then captures an ultrasound image of the breast while maintaining the compressed state is performed, performs control to set a force of the compression member compressing the breast to a first force in the capture of the radiographic image and to change the force of the compression member compressing the breast from the first force to a second force lower than the first force in the capture of the ultrasound image.

According to a second aspect of the present disclosure, in the control device according to the first aspect, the second force may be set such that an amount of change in a thickness of the breast in a case in which the compressed state is changed from a state in which the breast is compressed with the first force to a state in which the breast is compressed with the second force is equal to or less than a predetermined amount of change.

According to a third aspect of the present disclosure, in the control device according to the first or second aspect, in a case in which the force is changed from the first force to the second force, the compression control unit may perform control to continuously reduce the force from the first force to the second force.

According to a fourth aspect of the present disclosure, in the control device according to the first or second aspect, in a case in which the first force is equal to or less than a predetermined value, the compression control unit may perform control to maintain the force of compressing the breast in the capture of the ultrasound image at the first force, instead of changing the force to the second force.

According to a fifth aspect of the present disclosure, the control device according to the first or second aspect may further comprise an acquisition unit that acquires mammary gland amount information indicating an amount of mammary gland in the breast. In a case in which the amount of mammary gland indicated by the mammary gland amount information is equal to or less than a predetermined amount of mammary gland, the compression control unit may perform control to change the force of compressing the breast in the capture of the ultrasound image from the first force to the second force. In a case in which the amount of mammary gland indicated by the mammary gland amount information is more than the predetermined amount of mammary gland, the compression control unit may perform control to maintain the force of compressing the breast in the capture of the ultrasound image at the first force, instead of changing the force to the second force.

According to a sixth aspect of the present disclosure, the control device according to the first or second aspect may further comprise an acquisition unit that acquires region information indicating a mammary gland region in the breast on the basis of the radiographic image. In a case in which a size of the mammary gland region indicated by the region information is equal to or less than a predetermined size, the compression control unit may perform control to change the force of compressing the breast in the capture of the ultrasound image from the first force to the second force. In a case in which the size of the mammary gland region indicated by the region information is greater than the predetermined size, the compression control unit may perform control to maintain the force of compressing the breast in the capture of the ultrasound image at the first force, instead of changing the force to the second force.

According to a seventh aspect of the present disclosure, the control device according to the first or second aspect may further comprise an acquisition unit that acquires mammary gland amount information indicating an amount of mammary gland in the breast. In a case in which the amount of mammary gland indicated by the mammary gland amount information is equal to or more than a predetermined amount of mammary gland, the compression control unit may perform control to change the force of compressing the breast in the capture of the ultrasound image from the first force to the second force. In a case in which the amount of mammary gland indicated by the mammary gland amount information is less than the predetermined amount of mammary gland, the compression control unit performs control to maintain the force of compressing the breast in the capture of the ultrasound image at the first force, instead of changing the force to the second force.

According to an eighth aspect of the present disclosure, the control device according to the first or second aspect may further comprise an acquisition unit that acquires region information indicating a mammary gland region in the breast on the basis of the radiographic image. In a case in which a size of the mammary gland region indicated by the region information is equal to or greater than a predetermined size, the compression control unit may perform control to change the force of compressing the breast in the capture of the ultrasound image from the first force to the second force. In a case in which the size of the mammary gland region indicated by the region information is less than the predetermined size, the compression control unit may perform control to maintain the force of compressing the breast in the capture of the ultrasound image at the first force, instead of changing the force to the second force.

According to a ninth aspect of the present disclosure, in the control device according to the first or second aspect, in a case in which the capture of the radiographic image is tomosynthesis imaging that irradiates the breast with radiation emitted from a radiation source at different irradiation angles and captures a radiographic image at each irradiation angle using a radiation detector, the compression control unit may perform control to change the force of compressing the breast in the capture of the ultrasound image from the first force to the second force. In a case in which the capture of the radiographic image is an imaging method other than the tomosynthesis imaging, the compression control unit may perform control to maintain the force of compressing the breast in the capture of the ultrasound image at the first force, instead of changing the force to the second force.

According to a tenth aspect of the present disclosure, in the control device according to any one of the first to ninth aspects, in a case in which a time for which the breast is compressed with the first force is equal to or greater than a predetermined value, the compression control unit may perform control to change the force of compressing the breast in the capture of the ultrasound image from the first force to the second force. In a case in which the time for which the breast is compressed with the first force is less than the predetermined value, the compression control unit may perform control to maintain the force of compressing the breast in the capture of the ultrasound image at the first force, instead of changing the force to the second force.

According to an eleventh aspect of the present disclosure, in the control device according to any one of the first to tenth aspects, the compression control unit may perform control to change the force from the first force to the second force by moving the compression member in a decompression direction.

According to a twelfth aspect of the present disclosure, in the control device according to any one of the first to eleventh aspects, the force of compressing the breast is a compression force of compressing the entire breast. The first force may be a first compression force and the second force may be a second compression force.

According to a thirteenth aspect of the present disclosure, in the control device according to any one of the first to eleventh aspects, the force of compressing the breast may be a compression pressure which is a compression force per unit area. The first force may be a first compression pressure and the second force may be a second compression pressure.

In order to achieve the object, according to a fourteenth aspect of the present disclosure, there is provided a radiography system comprising: a mammography apparatus that includes a radiation source, a radiation detector, and a compression member that compresses a breast disposed between the radiation source and the radiation detector and captures a radiographic image of the breast in the compressed state using the radiation detector; and the control device according to any one of the first to thirteenth aspects that controls the mammography apparatus.

In order to achieve the object, according to a fifteenth aspect of the present disclosure, there is provided a medical imaging system comprising: the radiography system according to the fourteenth aspect; and an ultrasonography apparatus that captures an ultrasound image of the breast compressed by the compression member of the mammography apparatus in the radiography system.

In order to achieve the object, according to a sixteenth aspect of the present disclosure, there is provided a medical imaging system comprising: a medical imaging apparatus that includes a radiation source, a radiation detector, and a compression member which compresses a breast disposed between the radiation source and the radiation detector, that captures a radiographic image of the breast in the compressed state using the radiation detector, and that captures an ultrasound image of the breast in the compressed state; and the control device according to any one of the first to thirteenth aspects that controls the medical imaging apparatus.

In order to achieve the object, according to a seventeenth aspect of the present disclosure, there is provided a control method including: capturing a radiographic image of a breast compressed by a compression member with a first force; changing the force of the compression member compressing the breast from the first force to a second force lower than the first force while maintaining the compressed state; and performing continuous imaging by capturing an ultrasound image of the breast compressed by the compression member with the second force.

In order to achieve the object, according to an eighteenth aspect of the present disclosure, there is provided a non-transitory storage medium storing a program that causes a computer to perform a control processing, the control processing including: capturing a radiographic image of a breast compressed by a compression member with a first force; changing the force of the compression member compressing the breast from the first force to a second force lower than the first force while maintaining the compressed state; and performing continuous imaging by capturing an ultrasound image of the breast compressed by the compression member with the second force.

A control device according to the present disclosure is a control device including a processor. In a case in which continuous imaging that captures a radiographic image of a breast compressed by a compression member and then captures an ultrasound image of the breast in the compressed state is performed, the processor performs control to set a force of the compression member compressing the breast to a first force in the capture of the radiographic image and to change the force of the compression member compressing the breast from the first force to a second force lower than the first force in the capture of the ultrasound image.

According to the present disclosure, it is possible to effectively relieve the pain of the subject.

DETAILED DESCRIPTION

Hereinafter, embodiments of the invention will be described in detail with reference to the drawings. Each of the embodiments does not limit the invention. In each of the embodiments, for example, a case in which an object of interest of the present disclosure is the mammary gland will be described.

First Embodiment

In this embodiment, an aspect in which a compression force of compressing the entire breast is an example of the force of compressing the breast according to the present disclosure will be described.

Figure 1:
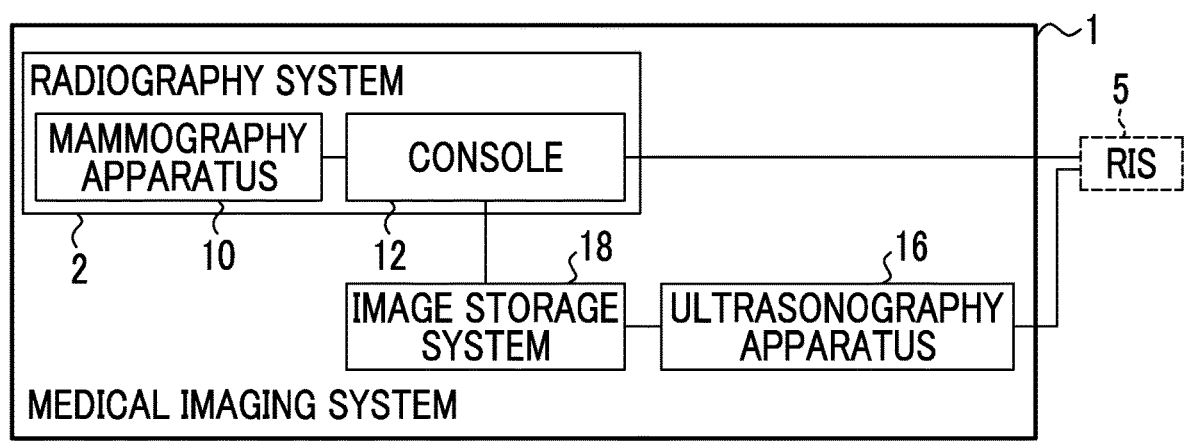
FIG. 1 is a diagram schematically illustrating an example of the overall configuration of a medical imaging system according to a first embodiment.

First, an example of the overall configuration of a medical imaging system according to this embodiment will be described. FIG. 1 is a diagram illustrating an example of the overall configuration of a medical imaging system 1 according to this embodiment.

As illustrated in FIG. 1, the medical imaging system 1 according to this embodiment comprises a radiography system 2, an ultrasonography apparatus 16, and an image storage system 18.

Figure 2:
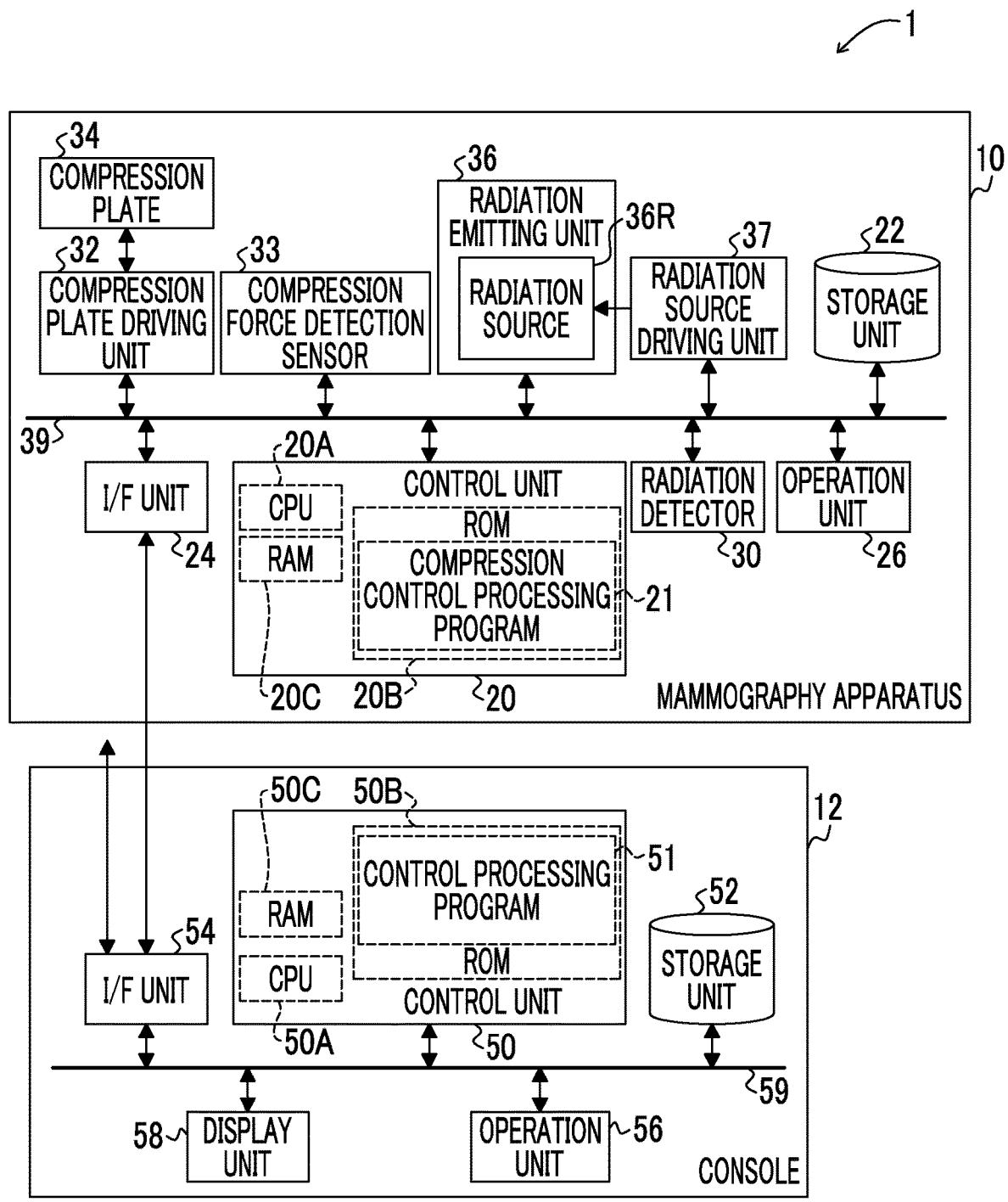
FIG. 2 is a block diagram illustrating an example of the configuration of a console and a mammography apparatus according to the first embodiment.
Figure 3:
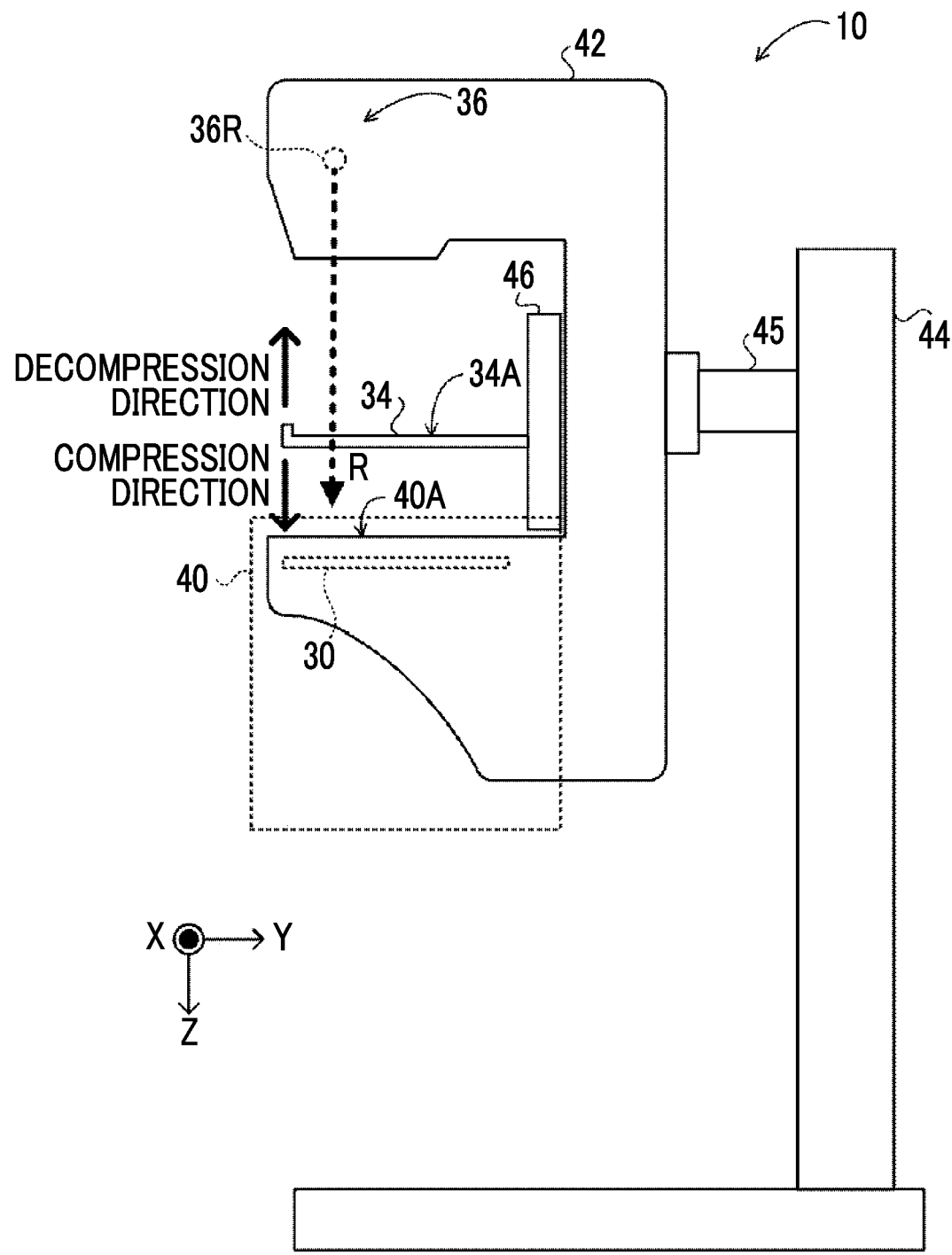
FIG. 3 is a side view illustrating an example of the outward appearance of the mammography apparatus according to the first embodiment.

First, the configuration of the radiography system 2 will be described. The radiography system 2 includes a mammography apparatus 10 and a console 12. FIG. 2 is a block diagram illustrating an example of the configuration of the mammography apparatus 10 and the console 12. FIG. 3 is a side view illustrating an example of the outward appearance of the mammography apparatus 10 according to this embodiment.

The mammography apparatus 10 according to this embodiment irradiates the breast of a subject as an object with radiation R (for example, X-rays) to capture a radiographic image of the breast. In addition, the mammography apparatus 10 may be an apparatus that captures the image of the breast of the subject not only in a state in which the subject stands up (standing state) but also in a state in which the subject sits on, for example, a chair (including a wheelchair) (sitting state).

As illustrated in FIG. 2, the mammography apparatus 10 according to this embodiment comprises a control unit 20, a storage unit 22, an interface (I/F) unit 24, an operation unit 26, a radiation detector 30, a compression plate driving unit 32, a compression force detection sensor 33, a compression plate 34, a radiation emitting unit 36, and a radiation source driving unit 37. The control unit 20, the storage unit 22, the I/F unit 24, the operation unit 26, the radiation detector 30, the compression plate driving unit 32, the compression force detection sensor 33, the radiation emitting unit 36, and the radiation source driving unit 37 are connected to each other through a bus 39, such as a system bus or a control bus, such that they can transmit and receive various kinds of information.

The control unit 20 according to this embodiment controls the overall operation of the mammography apparatus 10 under the control of the console 12. The control unit 20 comprises a central processing unit (CPU) 20A, a read only memory (ROM) 20B, and a random access memory (RAM) 20C. For example, various programs including a compression control processing program 21 which is executed by the CPU 20A and performs control related to the capture of a radiographic image are stored in the ROM 20B in advance. The RAM 20C temporarily stores various kinds of data.

The radiation detector 30 detects the radiation R transmitted through the breast which is the object. As illustrated in FIG. 3, the radiation detector 30 is provided in an imaging table 40. In the mammography apparatus 10 according to this embodiment, in a case in which imaging is performed, the breast of the subject is positioned on an imaging surface 40A of the imaging table 40 by a user such as a doctor or a radiology technician. For example, the imaging surface 40A with which the breast of the subject comes into contact is made of carbon in terms of the transmission and intensity of the radiation R.

The radiation detector 30 detects the radiation R transmitted through the breast of the subject and the imaging table 40, generates a radiographic image on the basis of the detected radiation R, and outputs image data indicating the generated radiographic image. The type of the radiation detector 30 according to this embodiment is not particularly limited. For example, the radiation detector 30 may be an indirect-conversion-type radiation detector that converts the radiation R into light and converts the converted light into charge or a direct-conversion-type radiation detector that directly converts the radiation R into charge.

For example, the image data of the radiographic image captured by the radiation detector 30 and various other kinds of information are stored in the storage unit 22. Examples of the storage unit 22 include a hard disk drive (HDD) and a solid state drive (SSD). The I/F unit 24 transmits and receives various kinds of information to and from the console 12 using wireless communication or wired communication. The image data of the radiographic image captured by the radiation detector 30 in the mammography apparatus 10 is transmitted to the console 12 through the I/F unit 24 by wireless communication or wired communication.

The operation unit 26 is provided as a plurality of switches in, for example, the imaging table 40 of the mammography apparatus 10. In addition, the operation unit 26 may be provided as a touch panel switch or may be provided as a foot switch that is operated by the user's feet.

The radiation emitting unit 36 comprises a radiation source 36R. As illustrated in FIG. 3, the radiation emitting unit 36 is provided in an arm portion 42 together with the imaging table 40 and a compression unit 46. In addition, as illustrated in FIG. 3, the mammography apparatus 10 according to this embodiment comprises the arm portion 42, a base 44, and a shaft portion 45. The arm portion 42 is supported by the base 44 so as to be movable in the up-down direction (Z-axis direction). The shaft portion 45 connects the arm portion 42 to the base 44. The radiation source driving unit 37 can relatively rotate the arm portion 42 with respect to the base 44, using the shaft portion 45 as a rotation axis.

Figure 4:
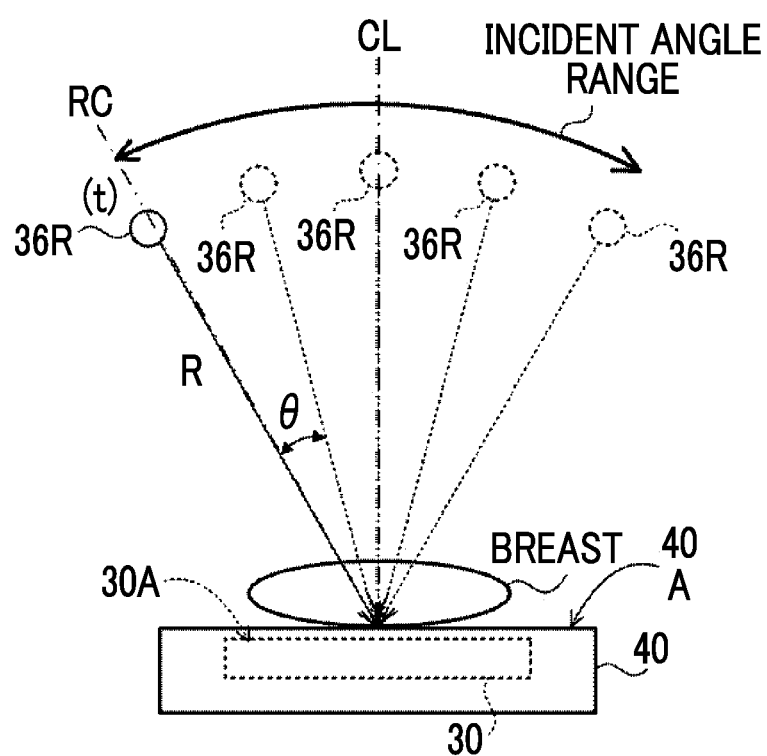
FIG. 4 is a diagram illustrating tomosynthesis imaging performed by the mammography apparatus according to the first embodiment.

In a case in which the mammography apparatus 10 performs tomosynthesis imaging, with the rotation of the arm portion 42, the radiation source 36R of the radiation emitting unit 36 is continuously moved to each of a plurality of irradiation positions with different irradiation angles (projection angles) by the radiation source driving unit 37. In this embodiment, as illustrated in FIG. 4, the radiation source 36R is moved to the irradiation positions t (t=0, 1, . . . , T; in FIG. 4, T=5) with different irradiation angles which are arranged at an interval of a predetermined angle θ, that is, the positions where the radiation R is incident on a detection surface 30A of the radiation detector 30 at different angles. At each irradiation position, the radiation R is emitted from the radiation source 36R in response to a command from the console 12 and the radiation detector 30 captures a radiographic image. In a case in which the radiography system 2 performs tomosynthesis imaging that moves the radiation source 36R to each irradiation position t and captures a projection image at each irradiation position t, T projection images are obtained. In this embodiment, the aspect in which the radiation emitting unit 36 is moved to move the radiation source 36R to the irradiation position t has been described. However, the present disclosure is not limited to this embodiment. For example, the mammography apparatus 10 may be configured to comprise a plurality of radiation sources 36R corresponding to each irradiation position t.

Figure 5:
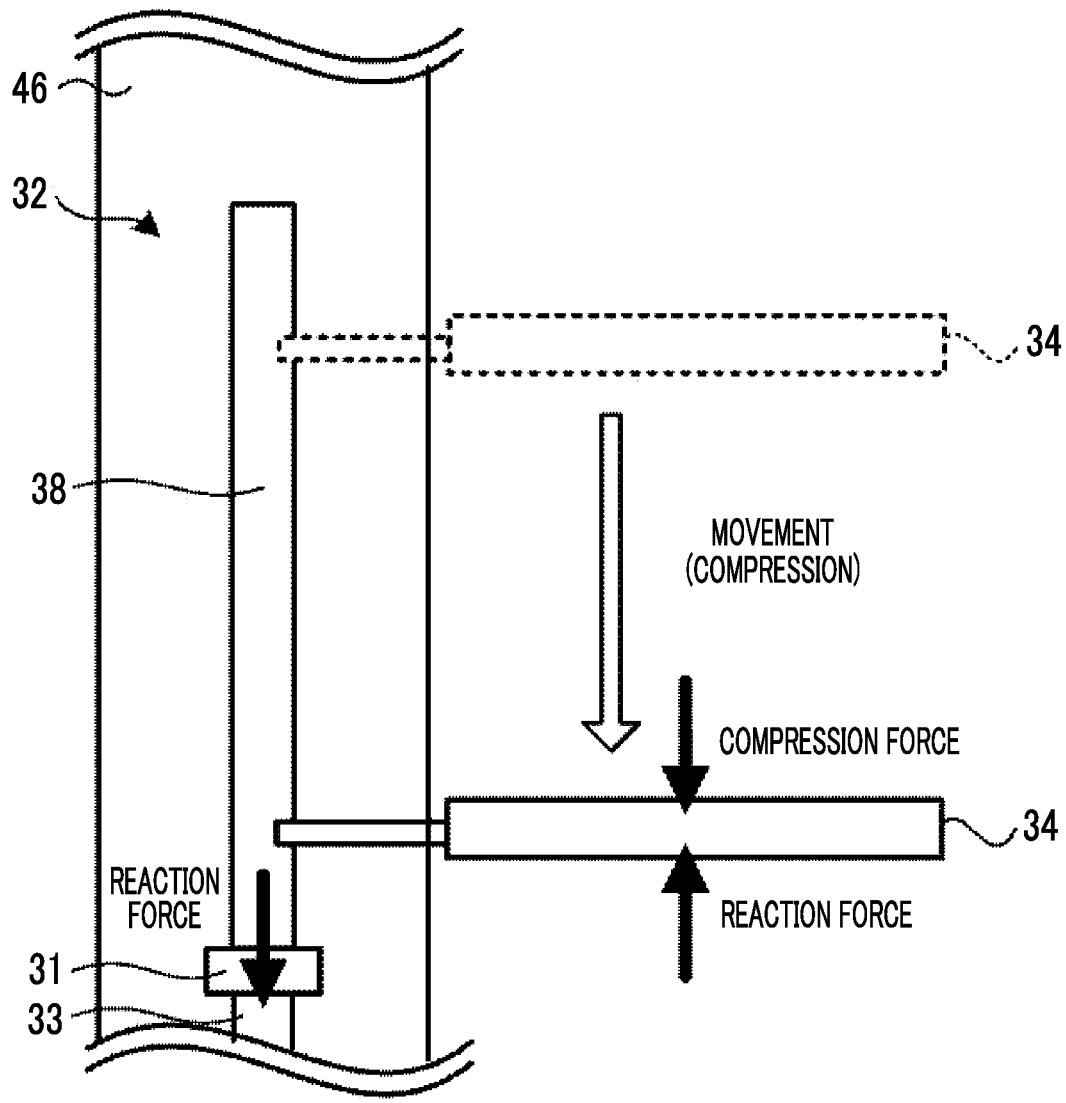
FIG. 5 is a diagram illustrating an example of a configuration in a case in which a compression force is detected by load applied to a motor in the first embodiment.

As illustrated in FIGS. 3 and 5, the compression plate driving unit 32, the compression force detection sensor 33, and the compression plate 34 are provided in the compression unit 46. Each of the compression unit 46 and the arm portion 42 can be relatively rotated with respect to the base 44, using the shaft portion 45 as a rotation axis. In this embodiment, gears (not illustrated) are provided in each of the shaft portion 45, the arm portion 42, and the compression unit 46. Each gear is switched between an engaged state and a disengaged state to connect each of the arm portion 42 and the compression unit 46 to the shaft portion 45. One or both of the arm portion 42 and the compression unit 46 connected to the shaft portion 45 are rotated integrally with the shaft portion 45.

The compression plate 34 according to this embodiment is a plate-shaped compression member and is moved in the up-down direction (Z-axis direction) by the compression plate driving unit 32 to compress the breast of the subject against the imaging table 40. As illustrated in FIG. 3, for the movement direction of the compression plate 34, the direction in which the breast is compressed, that is, the direction in which the compression plate 34 becomes closer to the imaging surface 40A is referred to as a "compression direction" and the direction in which the compression of the breast is released, that is, the direction in which the compression plate 34 becomes closer to the radiation emitting unit 36 is referred to as a "decompression direction".

As illustrated in FIG. 5, the compression unit 46 comprises the compression plate driving unit 32 including a motor 31 and a ball screw 38 and the compression force detection sensor 33. The compression force detection sensor 33 has a function of detecting the compression force of the compression plate 34 against the entire breast. In the example illustrated in FIG. 5, the compression force detection sensor 33 detects the compression force on the basis of the load applied to the motor 31 as a driving source of the compression plate 34. The compression plate 34 is supported by the ball screw 38 and the motor 31 is driven to slide the compression plate 34 between the imaging table 40 and the radiation source 36R. The compression force detection sensor 33 according to this embodiment is a strain gauge, such as a load cell. The compression force detection sensor 33 detects reaction force to the compression force of the compression plate 34 to detect the compression force of the compression plate 34 against the breast.

A method for detecting the compression force is not limited thereto. For example, the compression force detection sensor 33 may be a semiconductor pressure sensor or a capacitive pressure sensor. Further, for example, the compression force detection sensor 33 may be provided in the compression plate 34.

It is preferable that the compression plate 34 is optically transparent in order to check positioning or a compressed state in the compression of the breast. In addition, the compression plate 34 is made of a material having high transmittance for the radiation R. It is desirable that the compression plate 34 is made of a material that facilitates the transmission of ultrasonic waves from an ultrasound probe 65 (see FIG. 7, which will be described in detail below) of the ultrasonography apparatus 16. Examples of the material forming the compression plate 34 include resins such as polymethylpentene, polycarbonate, acrylic, and polyethylene terephthalate. In particular, polymethylpentene is suitable as the material forming the compression plate 34 since it has low rigidity, high elasticity, and high flexibility and has suitable values for acoustic impedance that affects the reflectance of ultrasonic waves and an attenuation coefficient that affects the attenuation of ultrasonic waves. The member forming the compression plate 34 is not limited to this embodiment. For example, the member forming the compression plate 34 may be a film-like member.

In this example, the compression plate 34 compresses the entire breast. However, the present disclosure is not limited thereto. The compression plate 34 may compress a part of the breast. In other words, the compression plate 34 may be smaller than the breast. For example, a compression plate 34 used for so-called spot imaging which captures a radiographic image of only a region in which a lesion exists is known as the compression plate 34.

Figure 6:
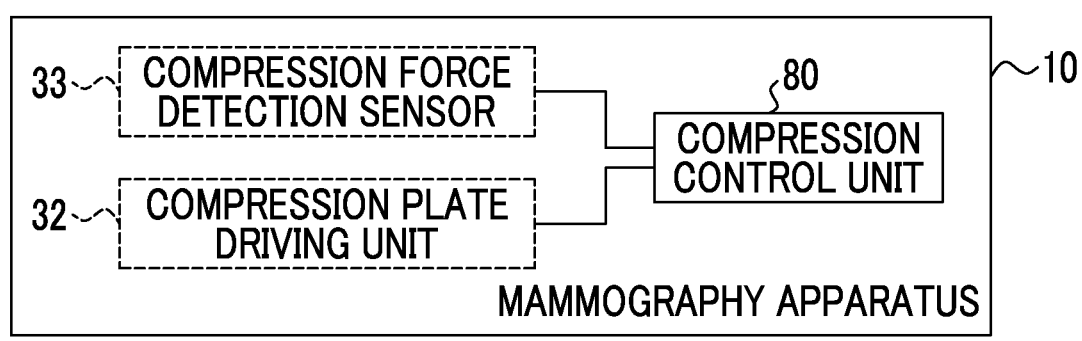
FIG. 6 is a functional block diagram illustrating an example of the function of the mammography apparatus according to the first embodiment.

FIG. 6 is a functional block diagram illustrating an example of the configuration of the mammography apparatus 10 according to this embodiment. As illustrated in FIG. 6, the mammography apparatus 10 according to this embodiment comprises a compression control unit 80. For example, in the mammography apparatus 10 according to this embodiment, the CPU 20A of the control unit 20 executes the compression control processing program 21 stored in the ROM 20B such that the control unit 20 functions as the compression control unit 80. The mammography apparatus 10 according to this embodiment is an example of a control device according to the present disclosure.

Information indicating the compression force which is the detection result of the compression force detection sensor 33 is input to the compression control unit 80 of the mammography apparatus 10. The compression control unit 80 outputs a command related to the movement of the compression plate 34 to the compression plate driving unit 32.

In a case in which continuous imaging that captures a radiographic image of the breast compressed by the compression plate 34 and then captures an ultrasound image of the breast in the compressed state is performed, the compression control unit 80 performs control to set the compression force of the compression plate 34 against the breast to first compression force in the capture of the radiographic image and to change the compression force of the compression plate 34 against the breast from the first compression force to a second compression force lower than the first compression force in the capture of the ultrasound image.

In some cases, the mammography apparatus 10 according to this embodiment performs continuous imaging which captures a radiographic image of the breast compressed by the compression plate 34 and then captures an ultrasound image of the breast. In the case of the continuous imaging, the imaging time for which the breast is continuously compressed by the compression plate 34 is long. Therefore, the compression control unit 80 sets the compression force in the capture of an ultrasound image to be lower than the compression force in the capture of a radiographic image such that the pain of the subject caused by the compression of the breast is relieved.

The console 12 according to this embodiment has a function of controlling the mammography apparatus 10 using, for example, an imaging order and various kinds of information acquired from a radiology information system (RIS) 5 through a wireless communication local area network (LAN) and commands input by the user through an operation unit 56.

For example, the console 12 according to this embodiment is a server computer. As illustrated in FIG. 2, the console 12 comprises a control unit 50, a storage unit 52, an I/F unit 54, the operation unit 56, and a display unit 58. The control unit 50, the storage unit 52, the I/F unit 54, operation unit 56, and the display unit 58 are connected to each other through a bus 59, such as a system bus or a control bus, such that they can transmit and receive various kinds of information.

The control unit 50 according to this embodiment controls the overall operation of the console 12. The control unit 50 comprises a CPU 50A, a ROM 50B, and a RAM 50C. For example, various programs including a control processing program 51 (which will be described below) executed by the CPU 50A are stored in the ROM 50B in advance. The RAM 50C temporarily stores various kinds of data.

For example, the image data of the radiographic image captured by the mammography apparatus 10 and various other kinds of information are stored in the storage unit 52. An HDD or an SSD is given as an example of the storage unit 52.

The operation unit 56 is used by the user to input, for example, commands which are related to the capture of a radiographic image and include a command to emit the radiation R or various kinds of information. Therefore, the operation unit 56 according to this embodiment includes at least an irradiation command button that is pressed by the user to input a command to emit the radiation R. The operation unit 56 is not particularly limited. Examples of the operation unit 56 include various switches, a touch panel, a touch pen, and a mouse. The display unit 58 displays various kinds of information. In addition, the operation unit 56 and the display unit 58 may be integrated into a touch panel display.

The I/F unit 54 transmits and receives various kinds of information to and from the mammography apparatus 10, the RIS 5, and the image storage system 18 using wireless communication or wired communication. In the radiography system 2 according to this embodiment, the console 12 receives the image data of the radiographic image captured by the mammography apparatus 10 from the mammography apparatus 10 through the I/F unit 54, using wireless communication or wired communication.

Figure 7:
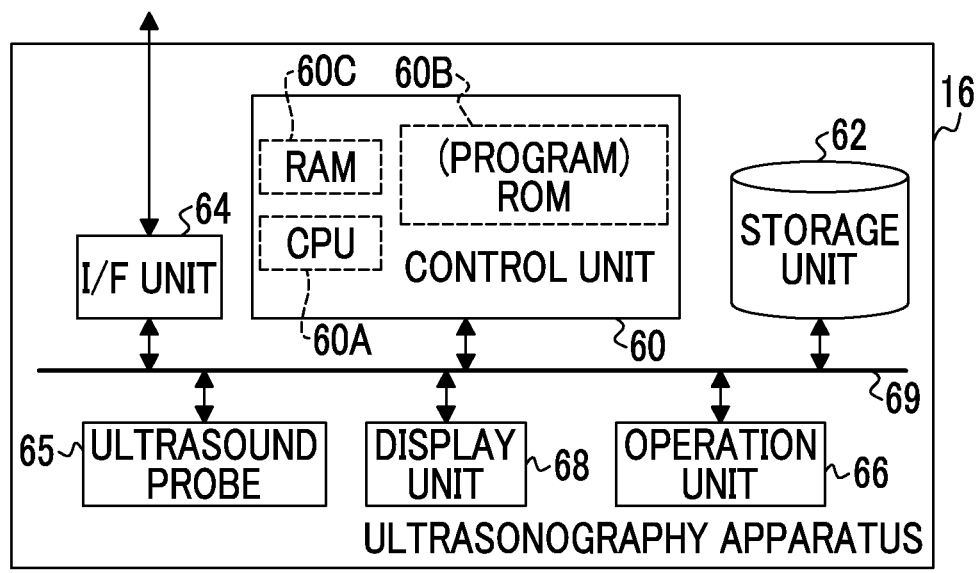
FIG. 7 is a block diagram illustrating an example of the configuration of an ultrasonography apparatus according to the first embodiment.

Next, the configuration of the ultrasonography apparatus 16 will be described. FIG. 7 is a block diagram illustrating an example of the configuration of the ultrasonography apparatus 16. The ultrasonography apparatus 16 is used by the user to capture an ultrasound image of the breast of the subject as the object and is a so-called hand-held ultrasonography apparatus.

As illustrated in FIG. 7, the ultrasonography apparatus 16 comprises a control unit 60, a storage unit 62, an I/F unit 64, the ultrasound probe 65, an operation unit 66, and a display unit 68. The control unit 60, the storage unit 62, the I/F unit 64, the ultrasound probe 65, the operation unit 66, and the display unit 68 are connected to each other through a bus 69, such as a system bus or a control bus, such that they can transmit and receive various kinds of information.

The control unit 60 according to this embodiment controls the overall operation of the ultrasonography apparatus 16. The control unit 60 comprises a CPU 60A, a ROM 60B, and a RAM 60C. For example, various programs executed by the CPU 60A are stored in the ROM 60B in advance. The RAM 60C temporarily stores various kinds of data.

For example, the image data of the captured ultrasound image and various other kinds of information are stored in the storage unit 62. A specific example of the storage unit 62 is an HDD or an SSD.

The ultrasound probe 65 is moved along the upper surface 34A (see FIG. 3, a surface opposite to the surface that comes into contact with the breast of the subject) of the compression plate 34 by the user and scans the breast with ultrasonic waves to acquire an ultrasound image of the breast. Specifically, in a case in which ultrasonography is performed, the ultrasound probe 65 is moved by the user along the upper surface 34A of the compression plate 34 in a state in which an acoustic matching member (not illustrated), such as echo jelly, is applied onto the upper surface 34A of the compression plate 34.

The ultrasound probe 65 comprises a plurality of ultrasound transducers (not illustrated) which are one-dimensionally or two-dimensionally arranged. Each of the ultrasound transducers transmits ultrasonic waves on the basis of an applied driving signal, receives ultrasound echoes, and outputs a received signal.

For example, each of the plurality of ultrasound transducers is a transducer configured by forming electrodes at both ends of a piezoelectric material (piezoelectric body), such as a piezoelectric ceramic typified by lead (Pb) zirconate titanate (PZT) or a polymeric piezoelectric element typified by polyvinylidene difluoride (PVDF). In a case in which a pulsed or continuous wave drive signal is transmitted to apply a voltage to the electrodes of the transducer, the piezoelectric body is expanded and contracted. Pulsed or continuous ultrasonic waves are generated from each transducer by the expansion and contraction and the ultrasonic waves are combined to form an ultrasound beam. Each transducer receives the propagated ultrasonic waves and is then expanded and contracted to generate an electric signal. The electric signal is output as an ultrasound received signal and is input to the main body (not illustrated) of the ultrasonography apparatus 16 through a cable (not illustrated).

The operation unit 66 is used by the user to input, for example, commands or various kinds of information related to the capture of an ultrasound image. The operation unit 66 is not particularly limited. Examples of the operation unit 66 include various switches, a touch panel, a touch pen, and a mouse. The display unit 68 displays, for example, various kinds of information or an ultrasound image corresponding to the received signal from the ultrasound probe 65. In addition, the operation unit 66 and the display unit 68 may be integrated into a touch panel display.

The I/F unit 64 transmits and receives various kinds of information to and from the RIS 5 and the image storage system 18 using wireless communication or wired communication. The image data of the ultrasound image captured by the ultrasonography apparatus 16 is transmitted to the image storage system 18 through the I/F unit 64 by wireless communication or wired communication.

Figure 8:
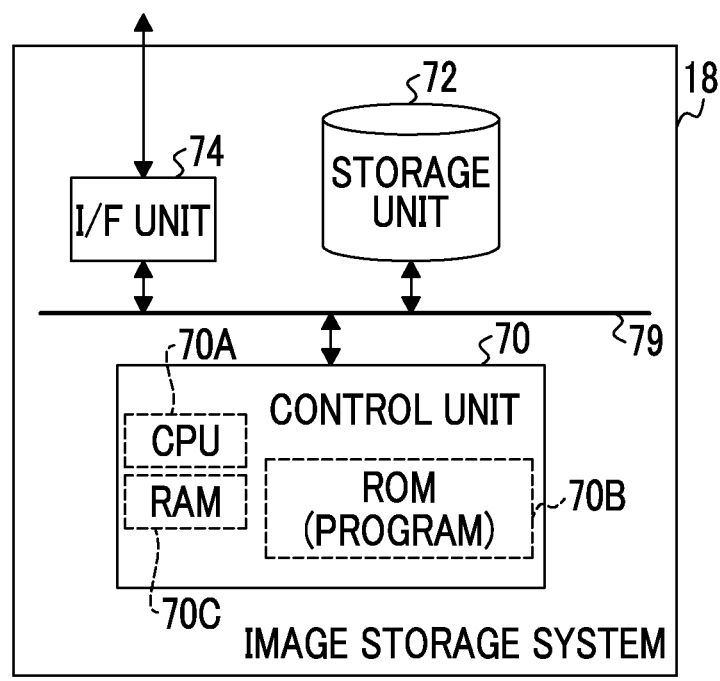
FIG. 8 is a block diagram illustrating an example of the configuration of an image storage system according to the first embodiment.

Next, the configuration of the image storage system 18 will be described. FIG. 8 is a block diagram illustrating an example of the configuration of the image storage system 18. The image storage system 18 stores the image data of the radiographic image captured by the radiography system 2 and the image data of the ultrasound image captured by the ultrasonography apparatus 16. The image storage system 18 extracts an image corresponding to a request from, for example, the console 12, the ultrasonography apparatus 16, and other reading devices (not illustrated) from the stored radiographic images and ultrasound images and transmits the extracted image to the apparatus which is the request source. A specific example of the image storage system 18 is a picture archiving and communication system (PAC S).

As illustrated in FIG. 8, the image storage system 18 comprises a control unit 70, a storage unit 72, and an I/F unit 74. The control unit 70, the storage unit 72, and the I/F unit 74 are connected to each other through a bus 79, such as a system bus or a control bus, such that they can transmit and receive various kinds of information.

The control unit 70 according to this embodiment controls the overall operation of the ultrasonography apparatus 16. The control unit 70 comprises a CPU 70A, a ROM 70B, and a RAM 70C. For example, various programs executed by the CPU 70A are stored in the ROM 70B in advance. The RAM 70C temporarily stores various kinds of data.

The storage unit 72 is a so-called database that stores each of the image data of the radiographic image and the image data of the ultrasound image so as to be associated with, for example, an imaging order or information released to the subject.

The I/F unit 74 has a function of transmitting and receiving various kinds of information to and from the console 12 and the ultrasonography apparatus 16 using wireless communication or wired communication.

Next, the operation of the mammography apparatus 10 according to this embodiment will be described with reference to the drawings.

For example, in a case in which the mammography apparatus 10 according to this embodiment receives an imaging order and an imaging start command from the console 12, the CPU 20A of the control unit 20 executes the compression control processing program 21 stored in the ROM 20B to perform the compression control process whose example is illustrated in FIG. 8. FIG. 8 is a flowchart illustrating an example of the flow of a compression control operation of the mammography apparatus 10 according to this embodiment.

First, in Step S100, the compression control unit 80 determines whether the user has input a compression command through the operation unit 26. In a case in which the mammography apparatus 10 according to this embodiment captures a radiographic image, first, the user positions the breast of the subject on the imaging surface 40A of the imaging table 40 of the mammography apparatus 10. In a case in which the positioning is completed, the user inputs a compression command through the operation unit 26. In a case in which a compression command has not been input, the determination result in Step S100 is "No". On the other hand, in a case in which a compression command has been input, the determination result in Step S100 is "Yes" and the process proceeds to Step S102.

Then, in Step S102, the compression control unit 80 directs the compression plate driving unit 32 to move the compression plate 34 in the compression direction in response to the compression command such that the breast is compressed with the first compression force between the compression plate 34 and the imaging surface 40A of the imaging table 40.

The compression of the breast by the compression plate 34 makes it possible to develop the overlap between the mammary gland tissues and to easily determine whether a lesion is a benign lesion or a malignant lesion. In addition, since the breast is compressed and fixed to the imaging table 40 by the compression plate 34, the body movement of the subject is suppressed. Therefore, it is possible to suppress the blurring of a radiographic image caused by the body movement. Further, since the breast is compressed by the compression plate 34, the thickness of the breast is reduced. Therefore, it is possible to reduce the amount of radiation emitted to the breast.

In a case in which the breast is fixed by the compression plate 34, the user presses an irradiation command button included in the operation unit 56 of the console 12 to input a command to emit the radiation R. In a case in which the irradiation command is input, the control unit 20 of the mammography apparatus 10 performs control such that the radiation R is emitted from the radiation source 37R to the breast compressed by the compression plate 34 under the control of the console 12. Then, the radiation detector 30 generates a radiographic image on the basis of the radiation R transmitted through the breast. The image data of the captured radiographic image is transmitted to the console 12.

Then, in Step S104, the compression control unit 80 determines whether the capture of a radiographic image has ended. For example, in a case in which the image data indicating the radiographic image captured by the radiation detector 30 has been transmitted to the console 12, the compression control unit 80 according to this embodiment determines that the capture of a radiographic image has ended. A method for determining whether the capture of a radiographic image has ended is not limited to this embodiment. For example, a command to end the capture of a radiographic image which has been input through the operation unit 56 of the console 12 may be received.

Until the capture of a radiographic image ends, the determination result in Step S104 is "No". On the other hand, in a case in which the capture of a radiographic image ends, the determination result in Step S104 is "Yes" and the process proceeds to Step S106.

In Step S106, the compression control unit 80 determines whether to capture an ultrasound image. For example, in a case in which a command to capture both a radiographic image and an ultrasound image is included in the imaging order or the user inputs a command to capture an ultrasound image through the operation unit 56, the compression control unit 80 according to this embodiment determines to capture an ultrasound image.

In a case in which an ultrasound image is not captured, the determination result in Step S106 is "No" and the process proceeds to Step S114. On the other hand, in a case in which an ultrasound image is captured, the determination result in Step S106 is "Yes" and the process proceeds to Step S108.

In Step S108, the compression control unit 80 determines whether to change the compression force. Specifically, the compression control unit 80 determines whether to change the compression force of compressing the breast from the first compression force to the second compression force.

The development of the mammary gland tissues may be little changed even in a case in which the compression force is reduced to the second compression force after the breast is compressed with the first compression force, which is disclosed in, for example, JP2017-225633A, JP2017-225634A, and JP2017-225635A. These patent publications disclose a technique in which, even in a case in which the compression plate 34 is moved in the decompression direction to reduce the compression force after the breast is compressed with the first compression force, it is difficult for the thickness of the breast to return to the original thickness. Since it is difficult for the thickness of the breast to return to the original thickness and it is possible to maintain the thickness of the breast, the development of the mammary gland tissues is maintained or is little changed.

The second compression force may be lower than the first compression force in order to relieve the pain of the subject. In a case in which the compression force against the breast is too low, the thickness of the breast may return to the original thickness and the development of the mammary gland tissues may be different. In a case in which the development of the mammary gland tissues is different between the capture of a radiographic image and the capture of an ultrasound image, for example, the position where calcification appears is changed, which is not preferable. In addition, in a case in which the compression force against the breast is too low, the body movement of the subject is likely to occur.

In a case in which the first compression force is relatively low, the second compression force lower than the first compression force may not be preferable for the above-mentioned reasons. Therefore, in the mammography apparatus 10 according to this embodiment, in a case in which the first compression force is equal to or less than a predetermined threshold value, the second compression force is considered to be too low and the capture of an ultrasound image is performed while the first compression force is maintained without being changed to the second compression force. Since the first compression force is relatively low, the pain of the subject is less than that in a case in which the first compression force is high.

According to the above-mentioned patent publications, the second compression force is preferably 40% to 70% of the first compression force and is more preferably 50% of the first compression force. Alternatively, the second compression force is preferably 40 N to 100 N lower than the first compression force and is more preferably 50 N lower than the first compression force. In other words, the first compression force is preferably 143% to 250% of the second compression force and is more preferably 200% of the second compression force. Alternatively, the first compression force is preferably 40 N to 100 N higher than the second compression force and is more preferably 60 N higher than the second compression force. In addition, according to the above-mentioned patent publications, it is preferable that the second compression force is in the range of 40 N to 100 N in order to effectively relieve the pain of the subject and to suppress the body movement of the subject.

Therefore, for example, in a case in which the second compression force decided according to the first compression force is equal to or less than a threshold value, the compression control unit 80 according to this embodiment determines not to change the second compression force. For example, the specific threshold value may be determined according to the preferable range of the second compression force, may be determined according to the thickness of the breast compressed by the compression plate 34, or may be experimentally obtained in advance.

In a case in which the second compression force is not changed, the determination result in Step S108 is "No" and the process proceeds to Step S112. On the other hand, in a case in which the second compression force is changed, the determination result in Step S108 is "Yes" and the process proceeds to Step S110.

In Step S110, the compression control unit 80 compresses the breast with the second compression force using the compression plate 34. Specifically, the compression control unit 80 directs the compression plate driving unit 32 to move the compression plate 34 in the decompression direction and to stop the movement of the compression plate 34 at the position where the compression force detected by the compression force detection sensor 33 is the second compression force.

Preferably, in a case in which the compression force of the compression plate 34 is not changed, the compression control unit 80 transmits information indicating that the compression force of the compression plate 34 is not changed to the console 12. Preferably, in a case in which the compression force of the compression plate 34 has been changed to the second compression force, the compression control unit 80 transmits information indicating that the change has been completed to the console 12.

In a case in which the information is received, preferably, the console 12 displays information indicating that the capture of an ultrasound image may be started on the display unit 58. In a case in which the capture of an ultrasound image is started while the compression control unit 80 changes the compression force, there is a concern that the pressure applied to the compression plate 34 will be changed and the detection accuracy of the compression force by the compression force detection sensor 33 will be reduced. As described above, since the timing when an ultrasound image is captured is presented, it is possible to prevent an ultrasound image from being captured while the compression force is changed, which is preferable.

The user operates the ultrasonography apparatus 16 to capture an ultrasound image of the breast. Specifically, the user applies an acoustic matching member (not illustrated), such as echo jelly, onto the upper surface 34A of the compression plate 34. The user operates the ultrasound probe 65 to scan the upper surface 34A of the compression plate 34 covered by the acoustic matching member with ultrasonic waves, thereby capturing an ultrasound image. The captured ultrasound image is displayed on the display unit 68 of the ultrasonography apparatus 16.

Then, in Step S112, the compression control unit 80 determines whether the capture of an ultrasound image has ended. For example, in the medical imaging system 1 according to this embodiment, in a case in which the capture of an ultrasound image ends, the user inputs a command to release the compression through the operation unit 26 of the mammography apparatus 10. In a case in which the command to release the compression has been input through the operation unit 26, the compression control unit 80 determines that the capture of an ultrasound image has ended.

In a case in which the capture of an ultrasound image has not ended, that is, in a case in which the command to release the compression has not been input, the determination result in Step S112 is "No". On the other hand, in a case in which the capture of an ultrasound image has ended, that is, in a case in which the command to release the compression has been input, the determination result in Step S112 is "Yes" and the process proceeds to Step S114.

In Step S114, the compression control unit 80 releases the compression of the breast by the compression plate 34 and ends the compression control process. Specifically, the compression control unit 80 directs the compression plate driving unit 32 to move the compression plate 34 in the decompression direction. The compression plate 34 is moved in the decompression direction to release the compression of the breast.

A method for determining whether to capture an ultrasound image in Step S106 of the compression control process in the compression control unit 80 is not limited to the above-mentioned method. For example, a method according to the following Modification Example 1 may be applied.

Modification Example 1

The compression control unit 80 of the mammography apparatus 10 transmits an inquiry whether to capture an ultrasound image to the console 12 and determines to capture an ultrasound image in a case in which a command to capture an ultrasound image is received as the result of the inquiry.

In addition, the timing when it is determined whether to capture an ultrasound image is not limited to the timing of Step S106. For example, it may be determined whether to capture an ultrasound image before the compression control process starts. In a case in which it is determined to capture an ultrasound image, the compression control process may be performed. In this case, the process of Step S106 may be omitted.

A method for determining whether to change the compression force of the compression plate 34 in Step S108 of the compression control process in the compression control unit 80 is not limited to the above-mentioned method. For example, methods according to the following Modification Examples 2 to 9 may be applied.

Modification Example 2

A correspondence relationship between the first compression force and whether to change the compression force to the second compression force may be determined in advance and the compression control unit 80 may determine whether to change the compression force of the compression plate 34 on the basis of correspondence relationship information indicating the correspondence relationship. In this case, for example, the correspondence relationship information may be stored in the storage unit 22 of the mammography apparatus 10 in advance or may be stored in the storage unit 52 of the console 12. For example, the compression control unit 80 may use the correspondence relationship information stored outside the radiography system 2.

Modification Example 3

The compression control unit 80 may determine whether to change the compression force of the compression plate 34 according to the time for which the breast is continuously compressed with the first compression force by the compression plate 34. In this embodiment, the time elapsed since the compression plate 34 starts to compress the breast with the first compression force may be measured. In a case in which the measured time is greater than a predetermined threshold value, the compression control unit 80 determines to change the compression force of the compression plate 34.

Modification Example 4

The compression control unit 80 may determine whether to change the compression force of the compression plate 34 according to the type of radiography. For example, in a case in which the type of radiography is tomosynthesis imaging, the imaging time may be longer than that in normal imaging. As the imaging time becomes longer, the time for which the breast is compressed by the compression plate 34 becomes longer. Therefore, the necessity of relieving the pain of the subject increases. In addition, in the case of the tomosynthesis imaging, the necessity of suppressing the body movement of the subject while a plurality of radiographic images are captured increases. Therefore, in some cases, the first compression force is relatively high. For this reason, the compression control unit 80 may determine to change the compression force of the compression plate 34 in a case in which the type of radiography is tomosynthesis imaging.

Modification Example 5

The compression control unit 80 may determine whether to change the compression force of the compression plate 34 in response to a command from the user. For example, in a case in which the subject has input a command to reduce the compression force through the operation unit 26 of the mammography apparatus 10, the compression force in the capture of an ultrasound image may be changed from the first compression force to the second compression force. In this case, for example, the subject may input the command to reduce the compression force before the capture of an ultrasound image starts, while a radiographic image is being captured, or after an ultrasound image is captured.

The way of feeling pain varies depending on the subject. According to this example, in a case in which the subject feels pain while being compressed with the first compression force, the subject may input the command to reduce the compression force.

Modification Example 6

The compression control unit 80 may determine whether to change the compression force of the compression plate 34 on the basis of the amount of mammary gland in the breast as the object. In a case in which the amount of mammary gland is relatively small, the amount of mammary gland tissues to be developed is small and deformation caused by compression is small. Therefore, for example, even in a case in which the thickness of the breast changes, the deviation of the mammary gland tissues is small. Conversely, in a case in which the amount of mammary gland is relatively large, the amount of mammary gland tissues to be developed is large and deformation caused by compression is large. Therefore, for example, in a case in which the thickness of the breast changes, the deviation of the mammary gland tissues increases. For this reason, in a case in which the amount of mammary gland in the breast is equal to or greater than a threshold value, the compression control unit 80 may determine to change the compression force of the compression plate 34.

A method for deriving the amount of mammary gland in the breast is not particularly limited. For example, the amount of mammary gland in the breast may be derived on the basis of a radiographic image captured in a state in which the breast is compressed with the first compression force by the compression plate 34. For example, a known method, such as a technique that estimates a mammary gland content on the basis of a radiographic image and a fat image estimated from the radiographic image described in JP2010-253245A, may be used as the method for deriving the amount of mammary gland from the radiographic image.

Figure 10:
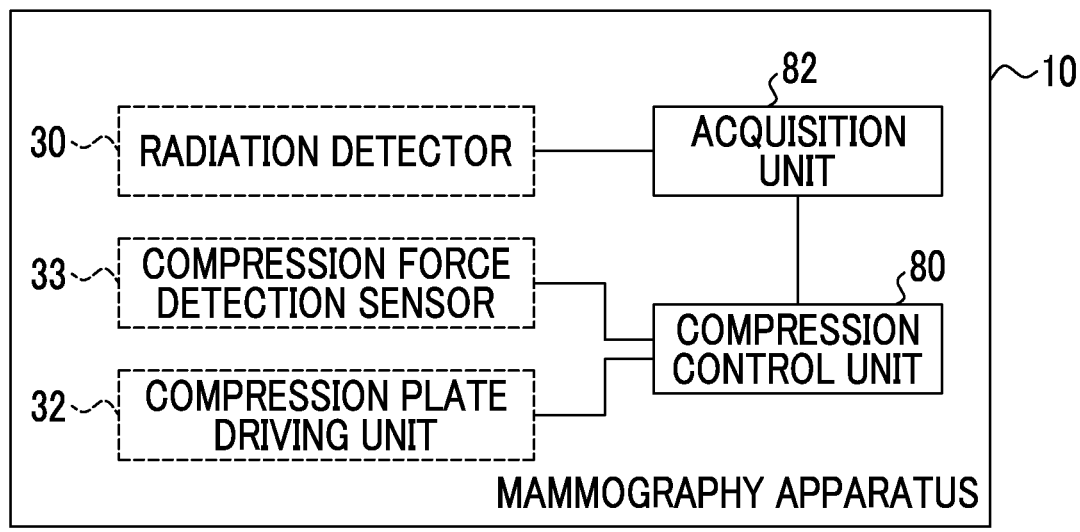
FIG. 10 is a functional block diagram illustrating an example of the function of mammography apparatuses according to Modification Examples 6 to 9.

FIG. 10 is a functional block diagram illustrating an example of the configuration of the mammography apparatus 10 in a case in which the amount of mammary gland is derived from a radiographic image. As illustrated in FIG. 10, the mammography apparatus 10 according to this modification example further comprises an acquisition unit 82. For example, in the mammography apparatus 10 according to this embodiment, the CPU 20A of the control unit 20 executes the compression control processing program 21 stored in the ROM 20B such that the control unit 20 functions as the acquisition unit 82.

The acquisition unit 82 acquires the amount of mammary gland from the radiographic image captured by the radiation detector 30 and outputs information indicating the amount of the amount of mammary gland to the compression control unit 80. The compression control unit 80 determines whether the amount of mammary gland is greater than a threshold value on the basis of the input information indicating the amount of mammary gland. In addition, for example, the amount of mammary gland may be derived from the radiographic image by the radiation detector 30 or the acquisition unit 82. Further, for example, the threshold value used for the determination by the compression control unit 80 may be experimentally obtained in advance. For example, the threshold value may vary depending on the thickness of the breast.

Modification Example 7

As the aspect in which the compression control unit 80 determines whether to change the compression force of the compression plate 34 on the basis of the amount of mammary gland in the breast as the object, the following aspect may be used: in a case in which the amount of mammary gland in the breast is equal to or less than the threshold value contrary to Modification Example 6, the compression control unit 80 determines to change the compression force of the compression plate 34.

In general, in the capture of an ultrasound image, the ultrasound probe 65 scans a mammary gland region. Therefore, as the mammary gland region becomes larger, the scanning range of the ultrasound probe 65 becomes wider and the imaging time becomes longer. As a result, the time for which the subject feels pain is likely to become longer. For this reason, in a case in which the amount of mammary gland in the breast is equal to or less than the threshold value, the compression control unit 80 may determine to change the compression force of the compression plate 34.

The configuration and the method described in Modification Example 6 may be applied as the configuration of the mammography apparatus 10 and a method for deriving the amount of mammary gland in this modification example.

Modification Example 6 and this modification example are opposite aspects. Therefore, for example, Modification Example 6 may be applied in a case in which importance is attached to the development of the mammary gland and Modification Example 7 may be applied in a case in which importance is attached to the pain of the subject. In addition, for example, any one of Modification Example 6 or Modification Example 7 may be applied according to the thickness of the breast compressed by the compression plate 34. The threshold value used in Modification Example 6 and the threshold value used in Modification Example 7 may be different values or the same value.

Modification Example 8

The compression control unit 80 may determine whether to change the compression force of the compression plate 34 according to the mammary gland region of the breast as the object. As the amount of mammary gland becomes larger, the size of the mammary gland region tends to become larger. As described in Modification Example 6, in a case in which the amount of mammary gland is large and the compression force is changed, the development of the mammary gland tissue may vary. Therefore, in a case in which the size of the mammary gland region is equal to or greater than the threshold value, the compression control unit 80 may determine to change the compression force of the compression plate 34.

A method for deriving the size of the mammary gland region is not particularly limited. For example, mammary gland tissue pixels corresponding to the mammary gland tissues are detected from the radiographic image and a region in which the number of detected mammary gland region pixels is equal to or greater than a predetermined value is derived as the mammary gland region. A method for detecting the mammary gland tissue pixel is not particularly limited. For example, a technique described in JP2010-253245A can be applied. In a case in which the technique described in this patent publication is applied, first, a radiographic image is divided into a breast image and a direct region. Then, a pectoral muscle region is extracted from the breast image. Then, the pectoral muscle region is removed from the breast image. Then, in the breast image from which the pectoral muscle region has been removed, a pixel in which the amount of transmission of the radiation R is equal to or less than a threshold value is detected as the mammary gland tissue region pixel.

For example, the configuration of the mammography apparatus 10 in a case in which the mammary gland region is derived may be the same as that illustrated in FIG. 10. In this case, the acquisition unit 82 acquires the size of the mammary gland region from the radiographic image captured by the radiation detector 30 and outputs information indicating the size of the mammary gland region to the compression control unit 80. The compression control unit 80 determines whether the size of the mammary gland region is greater than the threshold value on the basis of the input information indicating the size of the mammary gland region. The size of the mammary gland region may be derived from the radiographic image by, for example, the radiation detector 30 or the acquisition unit 82. For example, the threshold value used for the determination by the compression control unit 80 may be experimentally obtained in advance. For example, the threshold value may vary depending on the thickness of the breast.

Modification Example 9

As the aspect in which the compression control unit 80 determines whether to change the compression force of the compression plate 34 on the basis of the size of the mammary gland region of the breast as the object, the following aspect may be used: in a case in which the size of the mammary gland region of the breast is equal to or less than the threshold value contrary to Modification Example 8, the compression control unit 80 determines to change the compression force of the compression plate 34.

As described in Modification Example 7, as the size of the mammary gland region becomes larger, the time required to capture an ultrasound image is likely to become longer. Therefore, in a case in which the size of the mammary gland region is equal to or less than the threshold value, the compression control unit 80 may determine to change the compression force of the compression plate 34.

The configuration and the method described in Modification Example 8 may be applied as the configuration of the mammography apparatus 10 and a method for deriving the amount of mammary gland in this modification example.

Modification Example 8 and this modification example are opposite aspects. Therefore, for example, Modification Example 8 may be applied in a case in which importance is attached to the development of the mammary gland and Modification Example 9 may be applied in a case in which importance is attached to the pain of the subject. In addition, for example, any one of Modification Example 8 or Modification Example 9 may be applied according to the thickness of the breast compressed by the compression plate 34. The threshold value used in Modification Example 8 and the threshold value used in Modification Example 9 may be different values or the same value.

In this embodiment, in the capture of an ultrasound image, the user moves the ultrasound probe 65 on the upper surface 34A of the compression plate 34, which results in a change in the compression force applied to the compression plate 34. Therefore, the compression control unit 80 may perform feedback control in order to maintain the second compression force or the first compression force on the basis of the change in the compression force detected by the compression force detection sensor 33.

Second Embodiment

Next, a second embodiment will be described in detail. In the first embodiment, the aspect in which the compression force against the entire breast is an example of the force of compressing the breast according to the present disclosure has been described. However, in this embodiment, an aspect in which compression pressure that is a compression force per unit area is an example of the force of compressing the breast according to the present disclosure will be described. In each of the above-described embodiments, the compression control unit 80 controls the compression force of the compression plate 34 against the breast. However, in this embodiment, the compression control unit 80 controls the compression pressure of the compression plate 34 against the breast.

Even in a case in which the breast is compressed with the same compression force, the pain of the subject with a large breast tends to be less than that of the subject with a small breast since the compression force is dispersed. For this reason, it is preferable to finely control the movement of the compression plate 34 according to the size of the breast. Therefore, the mammography apparatus 10 according to this embodiment controls the compression of the breast by the compression plate 34 on the basis of the compression pressure that is the compression force per unit area, instead of the compression force of the compression plate 34 against the entire breast.

Since the overall configuration (see FIG. 1) of a medical imaging system 1 according to this embodiment is the same as that in the first embodiment, the description thereof will not be repeated. In this embodiment, since the configuration of the mammography apparatus 10 is partially different from the configuration of the mammography apparatus 10 according to the first embodiment, the different configuration will be described.

Figure 11:
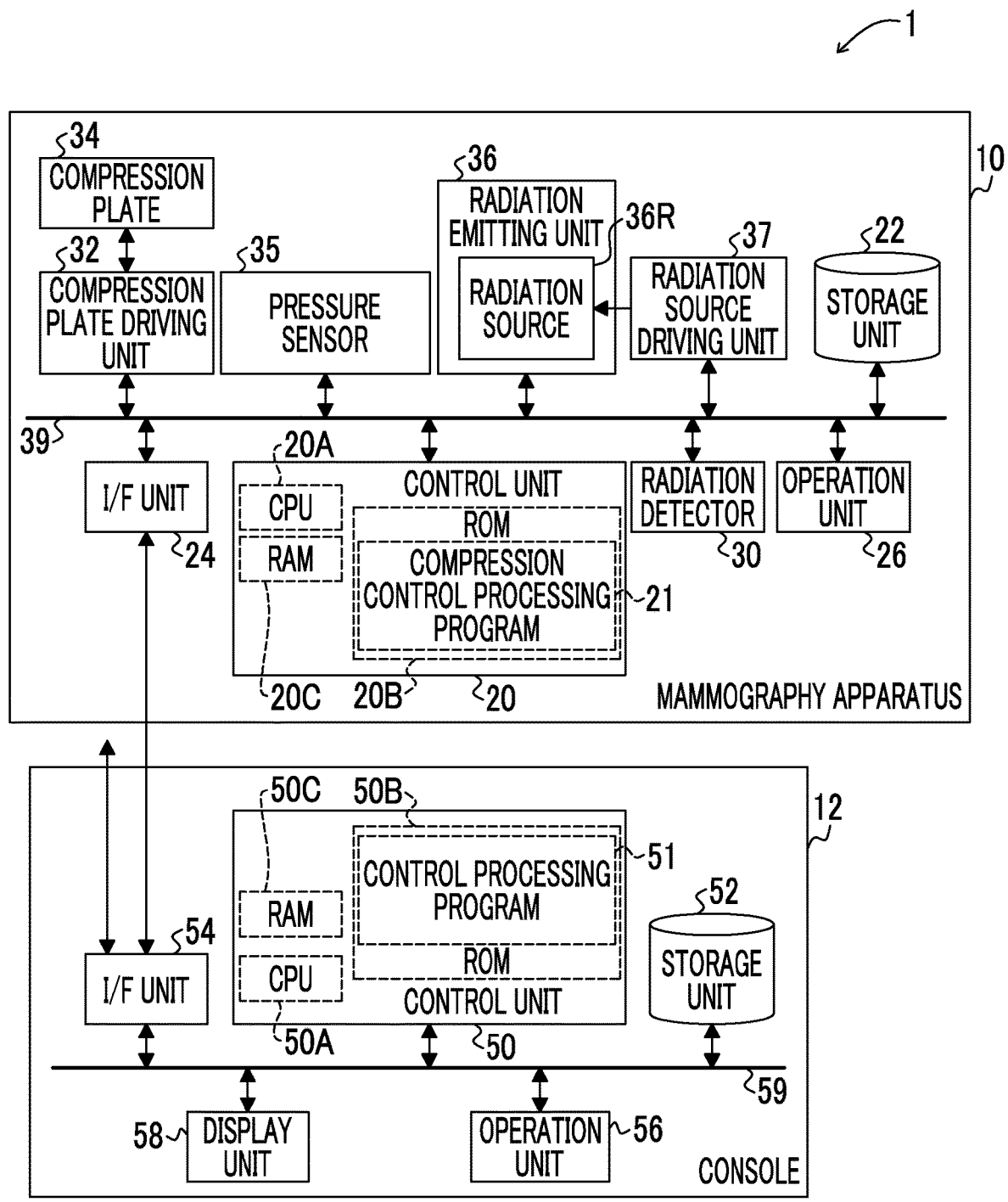
FIG. 11 is a block diagram illustrating an example of the configuration of a console and a mammography apparatus according to a second embodiment.

FIG. 11 is a block diagram illustrating an example of the configuration of the mammography apparatus 10 and the console 12 according to this embodiment. As illustrated in FIG. 11, the mammography apparatus 10 according to this embodiment differs from the mammography apparatus 10 according to the first embodiment in that it comprises a pressure sensor 35 instead of the compression force detection sensor 33.

Figure 12:
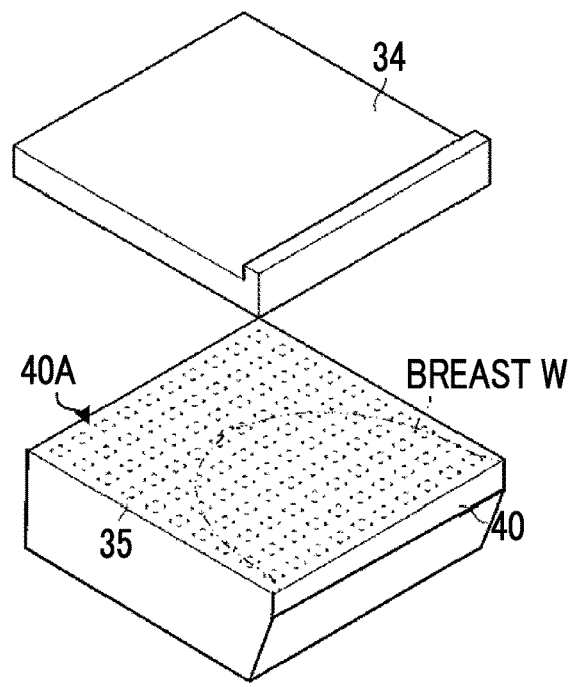
FIG. 12 is a diagram illustrating a pressure sensor.

As illustrated in FIG. 12, n (50 in this embodiment) pressure sensors 35 are two-dimensionally arranged on the imaging surface 40A of the imaging table 40 and each pressure sensor 35 detects the pressure applied to the imaging table 40 in a case in which the breast is compressed by the compression plate 34. The size of a region in which each pressure sensor 35 according to this embodiment detects pressure (the area of the imaging surface 40A; hereinafter, referred to as a "pressure detection area") is predetermined.

It is preferable that the pressure sensor 35 is made of a material which transmits the radiation R. In a case in which the pressure sensor 35 is made of a material which absorbs a portion of the radiation R, the image data of the acquired radiographic image is corrected according to the radiation transmittance of the pressure sensor 35.

An example of the functional configuration of the mammography apparatus 10 according to this embodiment is the same as that of the mammography apparatus 10 (see FIG. 6) according to the first embodiment except the operation of the compression control unit 80.

Figure 13:
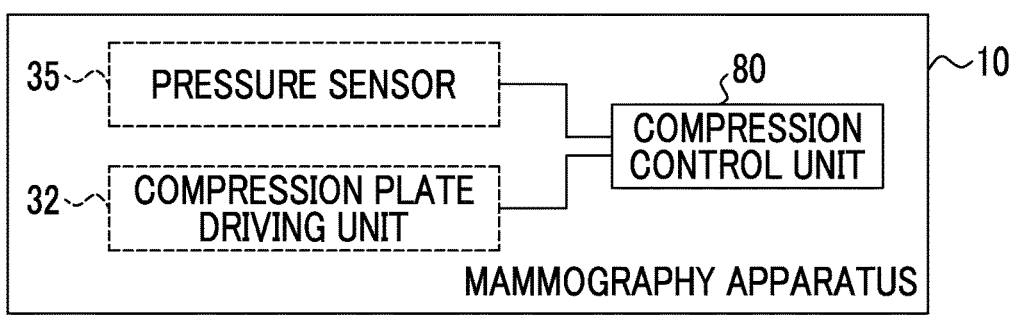
FIG. 13 is a functional block diagram illustrating an example of the function of a mammography apparatus according to a second embodiment.

FIG. 13 is a functional block diagram illustrating an example of the configuration of the mammography apparatus 10 according to this embodiment. As illustrated in FIG. 13, the mammography apparatus 10 according to this embodiment comprises the compression control unit 80 similarly to the mammography apparatus 10 (see FIG. 6) according to the first embodiment.

Information indicating the pressure which is the detection result of the pressure sensor 35 is input to the compression control unit 80 according to this embodiment. The compression control unit 80 outputs a command related to the movement of the compression plate 34 to the compression plate driving unit 32.

In a case in which the continuous imaging that captures a radiographic image of the breast compressed by the compression plate 34 and then captures an ultrasound image of the breast in the compressed state is performed, the compression control unit 80 performs control to set the compression pressure of the compression member against the breast to a first compression pressure in the capture of the radiographic image and to change the compression pressure of the compression plate 34 against the breast from the first compression pressure to a second compression pressure lower than the first compression pressure in the capture of the ultrasound image.

The compression control unit 80 according to this embodiment derives the compression pressure on the basis of the detection results acquired from each pressure sensor 35. A method for deriving the compression pressure is not particularly limited. For example, the compression control unit 80 may select the maximum value from the detection results of the n pressure sensors 35 and may derive the compression pressure on the basis of the selected maximum value and the pressure detection area. For example, the compression control unit 80 may select a predetermined number of detection results in descending order from the detection results of the n pressure sensors 35 and may derive the compression pressure on the basis of the average value of the selected detection results and the pressure detection area. For example, since the detection results of the pressure sensors 35 provided in a portion of the imaging surface 40A with which the breast does not come into contact change little from 0 N/mm$^2$, the compression control unit 80 may derive the compression pressure on the basis of the pressure detection area and the average value of the detection results except 0 N/mm$^2$ or the detection results in a predetermined range from 0 N/mm$^2$ in consideration of errors. As such, it is preferable to derive the compression pressure on the basis of the detection results of the pressure sensors 35 provided in a portion of the imaging surface 40A with which the breast comes into contact.

The compression control unit 80 according to this embodiment repeatedly acquires the detection results of the pressure sensors 35 at a predetermined interval (0.1 seconds in this embodiment) and directs the compression plate driving unit 32 to move the compression plate 34 in the compression direction or the decompression direction until the compression pressure derived on the basis of the detection results of the pressure sensors 35 reaches the first compression pressure or the second compression pressure.

Figure 9:
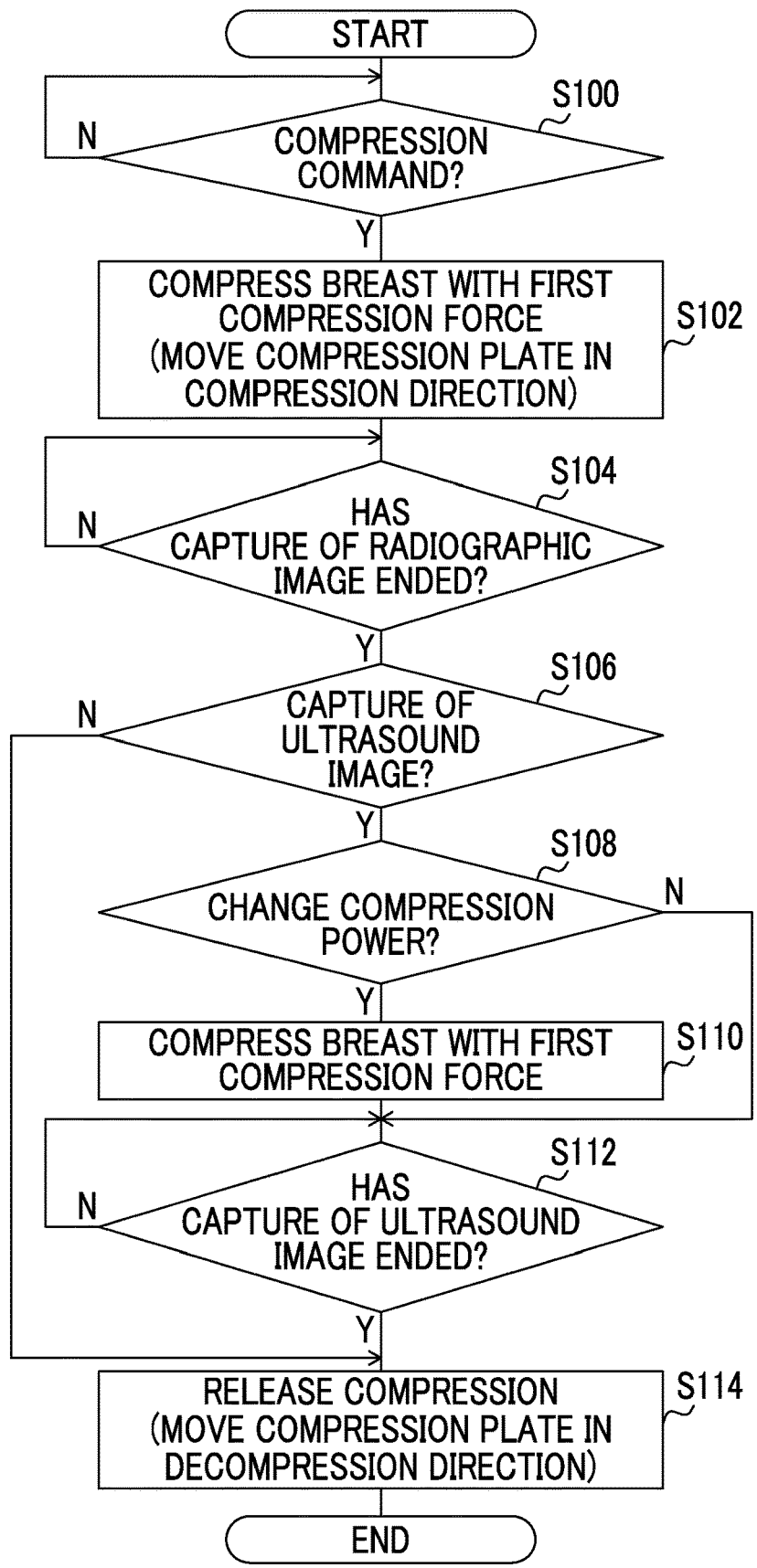
FIG. 9 is a flowchart illustrating an example of the flow of a compression control process of the mammography apparatus according to the first embodiment.

A compression control process of the compression control unit 80 in the mammography apparatus 10 according to this embodiment may be performed by changing the compression force in the compression control process (see FIG. 9) of the compression control unit 80 according to the first embodiment to the compression pressure. Since the overall flow of the compression control process according to this embodiment and processes in each step are the same as those in the first embodiment, the description thereof will not be repeated.

Third Embodiment

Figure 14:
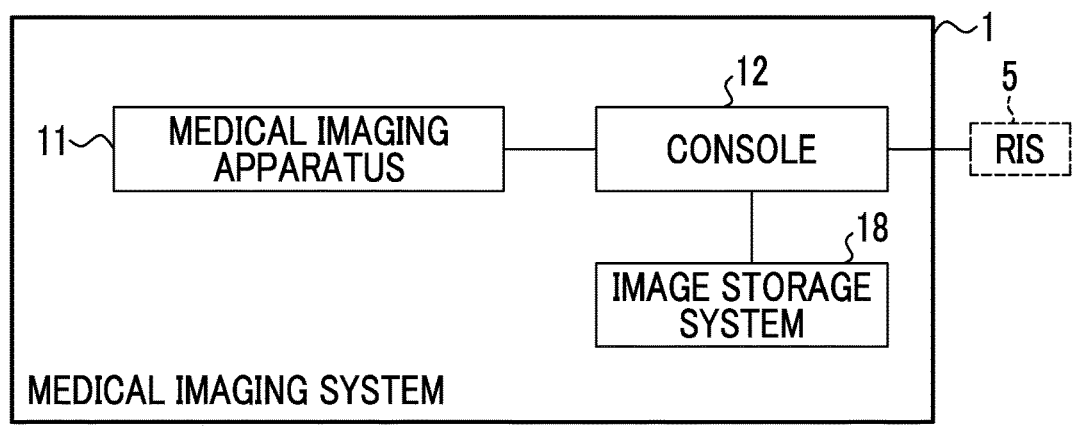
FIG. 14 is a diagram schematically illustrating an example of the overall configuration of a medical imaging system according to a third embodiment.

Next, a third embodiment will be described in detail. FIG. 14 is a diagram illustrating an example of the overall configuration of a medical imaging system 1 according to this embodiment. As illustrated in FIG. 14, the medical imaging system 1 according to this embodiment differs from the medical imaging system 1 (see FIG. 1) according to the first embodiment in that it comprises a medical imaging apparatus 11 instead of the mammography apparatus 10 and the ultrasonography apparatus 16.

The medical imaging apparatus 11 is an apparatus that is configured by combining the mammography apparatus 10 and the ultrasonography apparatus 16 according to the first embodiment, that is, an apparatus that can capture a radiographic image and an ultrasound image of the breast. For example, the medical imaging apparatus 11 according to this embodiment is a mammography apparatus that can automatically capture an ultrasound image.

Figure 15:
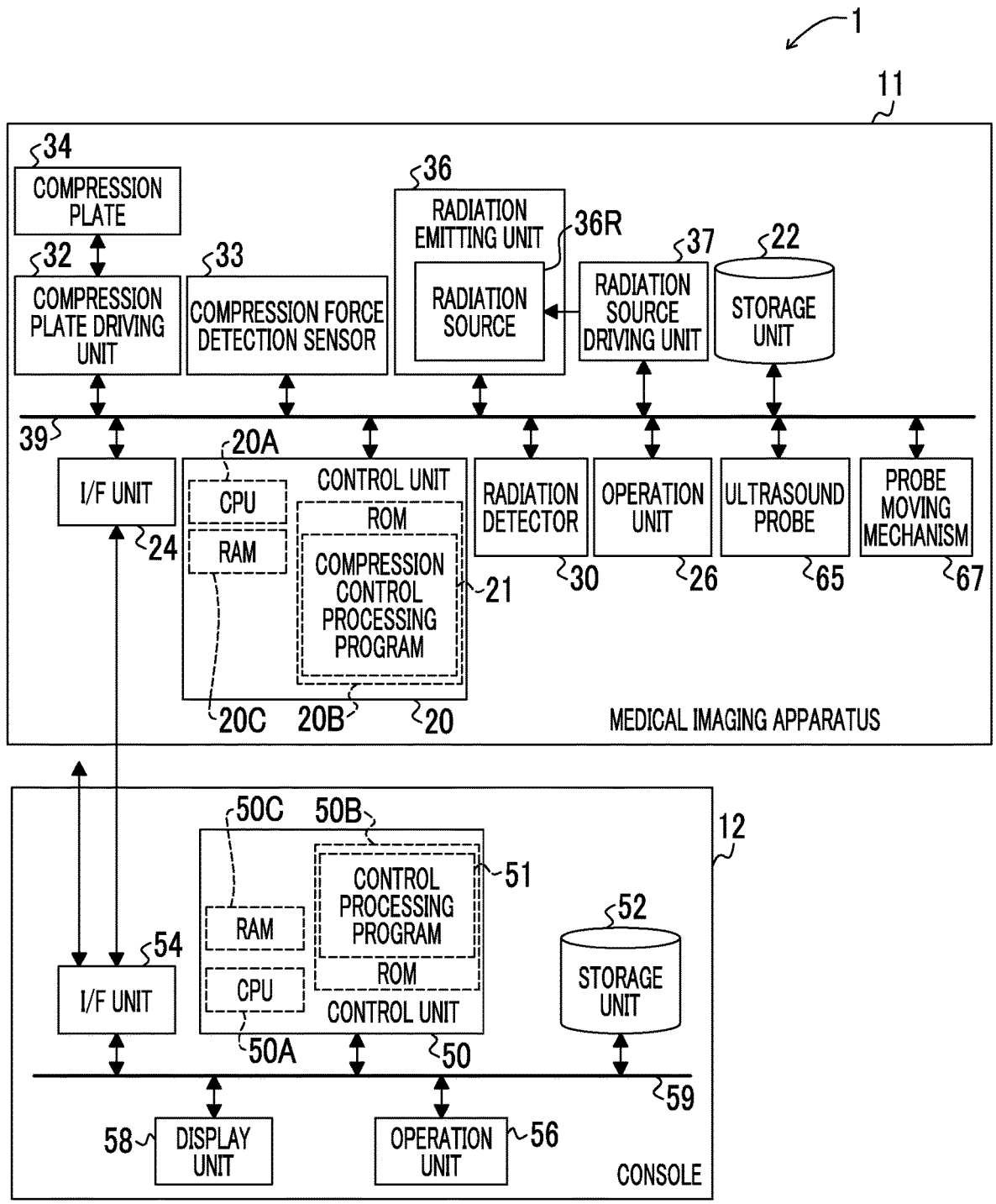
FIG. 15 is a block diagram illustrating an example of the configuration of a console and a medical imaging apparatus according to the third embodiment.
Figure 16:
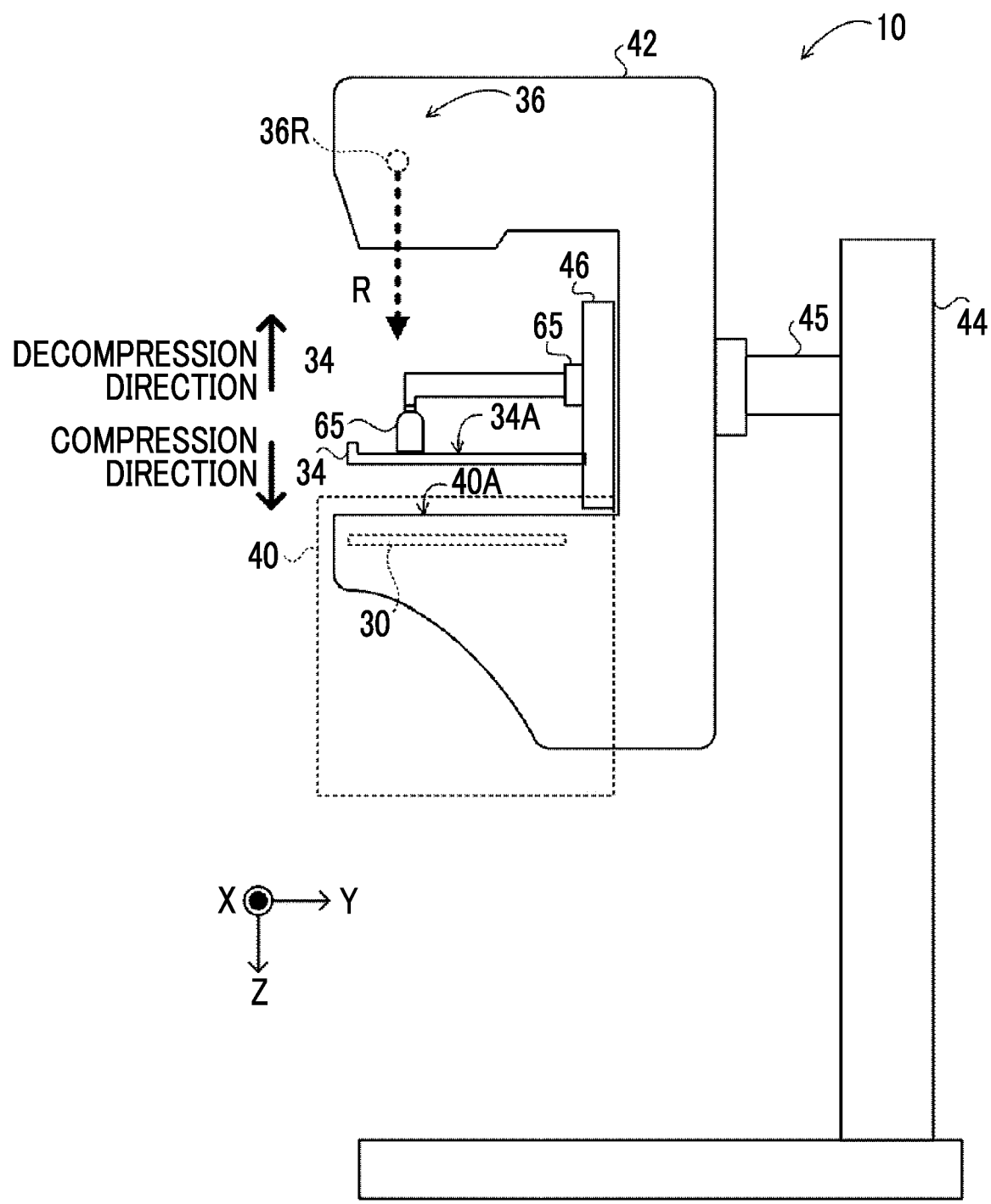
FIG. 16 is a side view illustrating an example of the outward appearance of the medical imaging apparatus according to the third embodiment.

FIG. 15 is a block diagram illustrating an example of the configuration of the medical imaging apparatus 11 and the console 12 according to this embodiment. As illustrated in FIG. 15, the medical imaging apparatus 11 according to this embodiment differs from the mammography apparatus 10 according to the first embodiment in that it further comprises an ultrasound probe 65 and a probe moving mechanism 67. As in an example illustrated in FIG. 16, the ultrasound probe 65 and the probe moving mechanism 67 are provided in the compression unit 46.

The ultrasound probe 65 is moved along the upper surface (a surface opposite to the surface on which the breast of the subject is placed) 34A of the compression plate 34 by the probe moving mechanism 67 and scans the breast with ultrasonic waves to acquire an ultrasound image of the breast. The ultrasound probe 65 is moved by the probe moving mechanism 67.

In a case in which an ultrasound image is captured, the compression control unit 80 controls the ultrasound probe 65 and the probe moving mechanism 67 in a state in which the breast is compressed by the compression plate 34. The compression control unit 80 checks the position of the ultrasound probe 65 moved by the probe moving mechanism 67 and directs the probe moving mechanism 67 to move the ultrasound probe 65. The compression control unit 80 transmits and receives ultrasonic waves to capture an ultrasound image while moving the ultrasound probe 65 using the probe moving mechanism 67.

The medical imaging apparatus 11 illustrated in FIG. 15 is an apparatus that scans the upper surface 34A of the compression plate 34 using the ultrasound probe 65 to capture an ultrasound image from the side of the radiation source 36R. However, the medical imaging apparatus 11 may be an imaging apparatus that captures an acoustic image from the opposite side, that is, the side of the imaging table 40.

Since the compression control process performed by the compression control unit 80 of the medical imaging apparatus 11 according to this embodiment is the same as the compression control process (see FIG. 9) performed by the compression control unit 80 according to the first embodiment, the description thereof will not be repeated. In this embodiment, since the medical imaging apparatus 11 captures an ultrasound image, it is possible to check the time required to capture the ultrasound image before the ultrasound image is captured. Therefore, the compression control unit 80 can check the time from the start of the capture of the radiographic image to the end of the capture of the ultrasound image before the ultrasound image is captured.

As described above, the mammography apparatus 10 or the medical imaging apparatus 11 according to each of the above-described embodiments comprises the compression control unit 80.

In a case in which the continuous imaging that captures a radiographic image of the breast compressed by the compression plate 34 and then captures an ultrasound image of the breast in the compressed state is performed, the compression control unit 80 performs control to set the compression force of the compression plate 34 against the breast to the first compression force in the capture of the radiographic image and to change the compression force of the compression plate 34 against the breast from the first compression force to the second compression force lower than the first compression force in the capture of the ultrasound image.

Alternatively, in a case in which the continuous imaging that captures a radiographic image of the breast compressed by the compression plate 34 and then captures an ultrasound image of the breast in the compressed state is performed, the compression control unit 80 performs control to set the compression pressure of the compression plate 34 against the breast to the first compression pressure in the capture of the radiographic image and to change the compression pressure of the compression plate 34 against the breast from the first compression pressure to the second compression pressure lower than the first compression pressure in the capture of the ultrasound image.

With the above-mentioned configuration, in a case in which the mammography apparatus 10 and the medical imaging apparatus 11 according to each of the above-described embodiments continuously captures a radiographic image and an ultrasound image in this order, the compression force or the compression pressure of the compression plate 34 against the breast is reduced. Therefore, according to the mammography apparatus 10 and the medical imaging apparatus 11, it is possible to effectively relieve the pain of the subject.

In each of the above-described embodiments, in a case in which the compression force or the compression pressure of the compression plate 34 is changed from the first compression force or the first compression pressure to the second compression force or the second compression pressure, the compression control unit 80 continuously reduces the compression force or the compression pressure, that is, reduces the compression force or the compression pressure without passing through the compression force or the compression pressure lower than the second compression force or the second compression pressure. However, the present disclosure is not limited to each of the above-described embodiments. The overlap of the mammary gland tissues is developed by compressing the breast as described above. Therefore, the compression control unit 80 can change the compression force or the compression pressure to the extent that the overlap of the mammary gland tissues, that is, the development of the mammary gland tissues is not changed or the amount of change is within an allowable range even though the overlap is changed. For example, as the compressed state of the breast for the time from the start of the capture of a radiographic image to the end of the capture of an ultrasound image, the breast may be continuously compressed to the extent that the area of the breast which comes into contact with the imaging surface 40A of the imaging table 40 is not changed. Therefore, the mammography apparatus 10 may reduce the compression against the breast according to the area of the breast which comes into contact with the imaging surface 40A after a radiographic image is captured and before an ultrasound image is captured.

In each of the above-described embodiments, the mammography apparatus 10 or the medical imaging apparatus 11 comprises the compression control unit 80 and functions as the control device according to the present disclosure. However, the apparatus comprising the compression control unit 80 is not limited to each of the above-described embodiments. For example, another apparatus, such as the console 12, in the medical imaging system 1 may have the functions of the compression control unit 80 and may function as the control device according to the present disclosure.

In each of the above-described embodiments, for example, the following various processors can be used as the hardware structure of processing units performing various processes such as the compression control unit 80 and the acquisition unit 82. The various processors include, for example, a programmable logic device (PLD), such as a field-programmable gate array (FPGA), that is a processor whose circuit configuration can be changed after manufacture and a dedicated electric circuit, such as an application specific integrated circuit (ASIC), that is a processor having a dedicated circuit configuration designed to perform a specific process, in addition to the CPU that is a general-purpose processor which executes software (program) to function as various processing units as described above.

One processing unit may be configured by one of the various processors or a combination of two or more processors of the same type or different types (for example, a combination of a plurality of FPGAs or a combination of a CPU and an FPGA). In addition, a plurality of processing units may be configured by one processor.

A first example of the configuration in which a plurality of processing units are configured by one processor is an aspect in which one processor is configured by a combination of one or more CPUs and software and functions as a plurality of processing units. A representative example of this aspect is a client computer or a server computer. A second example of the configuration is an aspect in which a processor that implements the functions of the entire system including a plurality of processing units using one integrated circuit (IC) chip is used. A representative example of this aspect is a system-on-chip (SoC). As such, various processing units are configured by using one or more of the various processors as a hardware structure.

In addition, specifically, an electric circuit (circuitry) obtained by combining circuit elements, such as semiconductor elements, can be used as the hardware structure of the various processors.

In each of the above-described embodiments, the aspect in which the compression control processing program 21 is stored (installed) in the ROM 20B in advance has been described. However, the invention is not limited thereto. The compression control processing program 21 may be recorded on a recording medium, such as a compact disk read only memory (CD-ROM), a digital versatile disk read only memory (DVD-ROM), or a universal serial bus (USB) memory, and then provided. In addition, the compression control processing program 21 may be downloaded from an external apparatus through the network.

For example, the configurations and operations of the medical imaging system 1, the radiography system 2, and the mammography apparatus 10 described in each of the above-described embodiments are illustrative and may be changed according to the situation, without departing from the scope and spirit of the invention. In addition, the above-described embodiments may be appropriately combined with each other.

Explanation of References

What is claimed is:

1. A control device comprising:
   a memory; and
   a processor that is coupled to the memory and configured to:
   in a case in which continuous imaging that captures a radiographic image of a breast compressed by a compression member and then captures an ultrasound image of the breast while maintaining the compressed state is performed, control to set a force of the compression member compressing the breast to a first force in the capture of the radiographic image and to change the force of the compression member compressing the breast from the first force to a second force lower than the first force in the capture of the ultrasound image; and
   on the basis of the radiographic image, acquire mammary gland amount information indicating an amount of mammary gland in the breast, or region information indicating a mammary gland region in the breast, the mammary gland region being determined by detecting mammary gland tissue pixels corresponding to mammary gland tissues from the radiographic image and determining a region in which a number of detected mammary gland region pixels is equal to or greater than a predetermined value as the mammary gland region,
   wherein the compression member comprises a plate-shaped compression member, and the second force is set to a force such that a development of mammary gland tissues compressed by the first force is substantially unchanged,
   wherein, in a case in which the amount of mammary gland indicated by the mammary gland amount information is equal to or less than a predetermined amount of mammary gland, or a size of the mammary gland region indicated by the region information is equal to or less than a predetermined size, the processor is configured to change the force of compressing the breast in the capture of the ultrasound image from the first force to the second force, and
   wherein, in a case in which the amount of mammary gland indicated by the mammary gland amount information is more than the predetermined amount of mammary gland, or the size of the mammary gland region indicated by the region information is greater than the predetermined size, the processor is configured to maintain the force of compressing the breast in the capture of the ultrasound image at the first force, instead of changing the force to the second force.

2. The control device according to claim 1,
   wherein the second force is set such that an amount of change in a thickness of the breast in a case in which the compressed state is changed from a state in which the breast is compressed with the first force to a state in which the breast is compressed with the second force is equal to or less than a predetermined amount of change.

3. The control device according to claim 1,
   wherein, in a case in which the force is changed from the first force to the second force, the processor is configured to directly reduce the force from the first force to the second force.

4. The control device according to claim 1,
   wherein, in a case in which the first force is equal to or less than a predetermined value, the processor is configured to maintain the force of compressing the breast in the capture of the ultrasound image at the first force, instead of changing the force to the second force.

5. The control device according to claim 1,
   wherein, in a case in which the capture of the radiographic image is tomosynthesis imaging that irradiates the breast with radiation emitted from a radiation source at different irradiation angles and captures a radiographic image at each irradiation angle using a radiation detector, the processor is configured to change the force of compressing the breast in the capture of the ultrasound image from the first force to the second force, and
   in a case in which the capture of the radiographic image is an imaging method other than the tomosynthesis imaging, the processor is configured to maintain the force of compressing the breast in the capture of the ultrasound image at the first force, instead of changing the force to the second force.

6. The control device according to claim 1,
   wherein, in a case in which a time for which the breast is compressed with the first force is equal to or greater than a predetermined value, the processor is configured to change the force of compressing the breast in the capture of the ultrasound image from the first force to the second force, and
   in a case in which the time for which the breast is compressed with the first force is less than the predetermined value, the processor is configured to maintain the force of compressing the breast in the capture of the ultrasound image at the first force, instead of changing the force to the second force.

7. The control device according to claim 1,
   wherein the processor is configured to change the force from the first force to the second force by moving the compression member in a decompression direction.

8. The control device according to claim 1,
   wherein the force of compressing the breast is a compression force of compressing the entire breast,
   the first force is a first compression force, and
   the second force is a second compression force.

9. The control device according to claim 1,
   wherein the force of compressing the breast is a compression pressure which is a compression force per unit area,
   the first force is a first compression pressure, and
   the second force is a second compression pressure.

10. A radiography system comprising:
    a mammography apparatus that includes a radiation source, a radiation detector, and a compression member that compresses a breast disposed between the radiation source and the radiation detector, and that captures a radiographic image of the breast in the compressed state using the radiation detector; and
    the control device according to claim 1 that controls the mammography apparatus.

11. A medical imaging system comprising:
the radiography system according to claim 10; and
an ultrasonography apparatus that captures an ultrasound image of the breast compressed by the compression member of the mammography apparatus in the radiography system.

12. A medical imaging system comprising:
a medical imaging apparatus that includes a radiation source, a radiation detector, and a compression member which compresses a breast disposed between the radiation source and the radiation detector, that captures a radiographic image of the breast in the compressed state using the radiation detector, and that captures an ultrasound image of the breast in the compressed state; and
the control device according to claim 1 that controls the medical imaging apparatus.

13. A control method comprising:
capturing a radiographic image of a breast compressed by a compression member with a first force;
on the basis of the radiographic image, acquiring mammary gland amount information indicating an amount of mammary gland in the breast, or region information indicating a mammary gland region in the breast, the mammary gland region being determined by detecting mammary gland tissue pixels corresponding to mammary gland tissues from the radiographic image and determining a region in which a number of detected mammary gland region pixels is equal to or greater than a predetermined value as the mammary gland region;
in a case in which the amount of mammary gland indicated by the mammary gland amount information is equal to or less than a predetermined amount of mammary gland, or a size of the mammary gland region indicated by the region information is equal to or less than a predetermined size, changing the force of the compression member compressing the breast from the first force to a second force lower than the first force while maintaining the compressed state;
in a case in which the amount of mammary gland indicated by the mammary gland amount information is more than the predetermined amount of mammary gland, or the size of the mammary gland region indicated by the region information is greater than the predetermined size, maintaining the force of the compression member compressing the breast at the first force; and
performing continuous imaging by capturing an ultrasound image of the breast compressed by the compression member,
wherein the compression member comprises a plate-shaped compression member, and the second force is set to a force such that a development of mammary gland tissues compressed by the first force is substantially unchanged.

14. A non-transitory storage medium storing a program that causes a computer to perform a control processing, the control processing comprising:
capturing a radiographic image of a breast compressed by a compression member with a first force;
on the basis of the radiographic image, acquiring mammary gland amount information indicating an amount of mammary gland in the breast, or region information indicating a mammary gland region in the breast, the mammary gland region being determined by detecting mammary gland tissue pixels corresponding to mammary gland tissues from the radiographic image and determining a region in which a number of detected mammary gland region pixels is equal to or greater than a predetermined value as the mammary gland region;
in a case in which the amount of mammary gland indicated by the mammary gland amount information is equal to or less than a predetermined amount of mammary gland, or a size of the mammary gland region indicated by the region information is equal to or less than a predetermined size, changing the force of the compression member compressing the breast from the first force to a second force lower than the first force while maintaining the compressed state;
in a case in which the amount of mammary gland indicated by the mammary gland amount information is more than the predetermined amount of mammary gland, or the size of the mammary gland region indicated by the region information is greater than the predetermined size, maintaining the force of the compression member compressing the breast at the first force; and
performing continuous imaging by capturing an ultrasound image of the breast compressed by the compression member,
wherein the compression member comprises a plate-shaped compression member, and the second force is set to a force such that a development of mammary gland tissues compressed by the first force is substantially unchanged.

* * * * *